US012642592B2

(12) United States Patent (10) Patent No.: US 12,642,592 B2
Murphy et al. (45) Date of Patent: Jun. 2, 2026

(54) SYSTEMS AND METHODS FOR DETERMINING LEG LENGTH CHANGE DURING HIP SURGERY

(71) Applicant: Stephen B. Murphy, Winchester, MA (US)

(72) Inventors: Stephen B. Murphy, Winchester, MA (US); William S. Murphy, Winchester, MA (US)

(73) Assignee: Stephen B. Murphy, Winchester, MA (US)

( * ) Notice: Subject to any disclaimer, the term of this patent is extended or adjusted under 35 U.S.C. 154(b) by 25 days.

(21) Appl. No.: 18/941,594

(22) Filed: Nov. 8, 2024

(65) Prior Publication Data

US 2025/0064525 A1 Feb. 27, 2025

Related U.S. Application Data

(63) Continuation of application No. 17/475,953, filed on Sep. 15, 2021, now Pat. No. 12,137,980, which is a
(Continued)

(51) Int. Cl.
*A61B 34/10* (2016.01)
*A61B 90/00* (2016.01)
(Continued)

(52) U.S. Cl.
CPC .............. *A61B 34/10* (2016.02); *A61B 90/37* (2016.02); *A61F 2/32* (2013.01); *A61F 2/4607* (2013.01);
(Continued)

(58) Field of Classification Search
None
See application file for complete search history.

(56) References Cited

U.S. PATENT DOCUMENTS 5,792,143 A 8/1998 Samuelson et al.
7,885,705 B2 2/2011 Murphy
(Continued)

FOREIGN PATENT DOCUMENTS

CN 103402450 A 11/2013
CN 104244860 A 12/2014
(Continued)

OTHER PUBLICATIONS

Wedemeyer, Christian, et al. "Digital templating in total hip arthroplasty with the Mayo stem." Archives of orthopaedic and trauma surgery 128.10 (2008): 1023-1029. (Year: 2008).*
(Continued)

*Primary Examiner* — Jason B Dunham
*Assistant Examiner* — Constantine Siozopoulos
(74) *Attorney, Agent, or Firm* — Cesari and McKenna, LLP

(57) ABSTRACT

Systems and methods facilitate the planning and performance of hip and other surgeries. A computer model of a hip may be generated and displayed. A template of a hip component that replaces a native portion of the hip may be superimposed on the model. Changes in leg length, offset, or anterior-posterior (AP) position as well as a virtual distance between a landmark on the model and a location on the template may be determined. During surgery, a physical distance corresponding to the virtual distance may be obtained. The template may be moved relative to the model to match the physical distance, and new change values in leg length, offset, or anterior-posterior (AP) position may be determined. The new change values may be evaluated, and the surgery may proceed, or the process may be repeated using templates corresponding to alternative components.

17 Claims, 20 Drawing Sheets

Related U.S. Application Data continuation of application No. 15/918,696, filed on Mar. 12, 2018, now Pat. No. 11,147,626.

(60) Provisional application No. 62/471,049, filed on Mar. 14, 2017.

(51) Int. Cl.
*A61F 2/32* (2006.01)
*A61F 2/46* (2006.01)

(52) U.S. Cl.
CPC ...... *A61F 2/4609* (2013.01); *A61B 2034/102* (2016.02); *A61B 2034/104* (2016.02); *A61B 2034/108* (2016.02); *A61B 2090/364* (2016.02); *A61F 2002/4633* (2013.01)

(56) References Cited

U.S. PATENT DOCUMENTS

| | | | |
|---|---|---|---|
| 8,428,698 B2 | 4/2013 | Meulink | |
| 9,138,319 B2 | 9/2015 | Fanson et al. | |
| 9,572,682 B2 | 2/2017 | Aghazadeh | |
| 11,147,626 B2 | 10/2021 | Murphy et al. | |
| 2007/0209220 A1 | 9/2007 | Murphy | |
| 2008/0183298 A1 | 7/2008 | McTighe et al. | |
| 2009/0270868 A1 | 10/2009 | Park et al. | |
| 2010/0191339 A1* | 7/2010 | Brooks | A61F 2/4657 |
| | | | 382/128 |
| 2011/0305379 A1 | 12/2011 | Mahfouz | |
| 2012/0008848 A1* | 1/2012 | Beck | G06T 7/60 |
| | | | 382/218 |
| 2012/0194505 A1 | 8/2012 | Beck | |
| 2013/0184831 A1 | 7/2013 | McMinn | |
| 2015/0238271 A1 | 8/2015 | Wollowick et al. | |
| 2015/0272695 A1 | 10/2015 | Kubiak et al. | |
| 2016/0100909 A1 | 4/2016 | Wollowick et al. | |
| 2018/0263699 A1 | 9/2018 | Murphy et al. | |
| 2022/0000562 A1 | 1/2022 | Murphy et al. | |

FOREIGN PATENT DOCUMENTS

| | | | | |
|---|---|---|---|---|
| WO | WO-2009062314 A1 * | 5/2009 | | A61B 5/103 |
| WO | WO-2012/080840 A1 | 6/2012 | | |
| WO | WO-2017/106858 A1 | 6/2017 | | |
| WO | WO-2017/160651 A1 | 9/2017 | | |

OTHER PUBLICATIONS

Chinese Search Report for Chinese Application No. 201880031998.8 dated Jul. 14, 2022, pp. 1-3.

Crooijmans, Hendrikus J.A., et al., "A New Digital Preoperative Planning Method for Total Hip Arthroplasties," Springer, Clinical Orthopaedics and Related Research 467.4, Apr. 2009, pp. 909-916.

Efe, Turgay, et al., "Precision of Preoperative Digital Templating in Total Hip Arthroplasty," Original Study, Acta Orthopaedica Belgica, Belgium, vol. 77, No. 5, Oct. 2011, pp. 616-621.

"European Search Report" European Application No. 23187493.4-1122/4252607, Applicant: Stephen B. Murphy, Date of Mailing: Feb. 28, 2024, pp. 1-9.

Harwood, David, MD, et al., "ANTHOLOGY: Primary Hip System Surgical Technique," Orthopaedics, Smith & Nephew, Inc., Aug. 2010, pp. 1-28.

"S-ROM Modular Hip System: Surgical Technique," DePuy Synthes Orthopaedics Inc., DePuy Synthes-Joint Reconstruction, Companies of Johnson & Johnson, Nov. 2013, pp. 1-24.

"Mako THA:Surgical Guide," Sep. 2015, Mako Surgical Corp. (Stryker), pp. 1-60.

"Materialise OrthoView: Complete Planning Solution for Hip Procedures," Meridian Technique Limited, 2014, pp. 1-6.

Michalikova, Monika, et al., "The Digital Pre-Operative Planning of Total Hip Arthroplasty," Acta Polytechnica Hungarica, vol. 7, No. 3, Oct. 2010, pp. 137-152.

Murphy, Stephen, et al., "Femoral Anteversion," The Journal of Bone and Joint Surgery, Incorporated, vol. 69-A, No. 8, Oct. 1987, pp. 1169-1176.

"Notification of Transmittal of the International Search Report and the Written Opinion of the International Searching Authority, or the Declaration," International Filing Date: Mar. 12, 2018, International Application No. PCT/US2018/021930, Applicant: Stephen B. Murphy, Date of Mailing: Jun. 18, 2018, pp. 1-16.

"OrthoView: Othopaedic Digital Imaging," User Guide Workstation System, Version 5.1, Issue 1.0, Aug. 2005, pp. 1-32.

"Profemur Preserve: Hip System-Surgical Technique," Wright Medical Technology, Inc., 2013, pp. 1-26.

Scheerlinck, Thierry, Primary Hip Arthroplasty Templating on Standard Radiogrpahs a Stepwise Approach, Aspects of Curent Management, Acta Orthopaedica Belgica, Belgium, vol. 76, No. 4, Aug. 2010, pp. 432-442.

Skinner, Harry, B., MD, PhD, et al., "ECHELON: Primary Hip System Surgical Technique," Smith & Nephew, Inc., Mar. 2015, pp. 1-28.

Slover, James, Erik Wetter, and Henrik Malchau, "Computer Templating of Hip Resurfacing Arthroplasty," Chapter 18, Modern Hip Resurfacing, Springer, London, 2009, pp. 185-188.

"TraumaCad-Version 2.4: Quick Start Guide," Voyant Health Ltd., Jul. 2014, pp. 1-11.

"TraumaCad-Version 2.5: Quick Start Guide," Brainlab Ltd., Feb. 2016, pp. 1-11.

"TraumaCad-Version 2.4: User's Guide," Brainlab Ltd., Dec. 2014, pp. 1-222.

"TraumaCad-Version 2.5: User's Guide," Voyant Health Ltd., Sep. 2017, pp. 1-179.

* cited by examiner

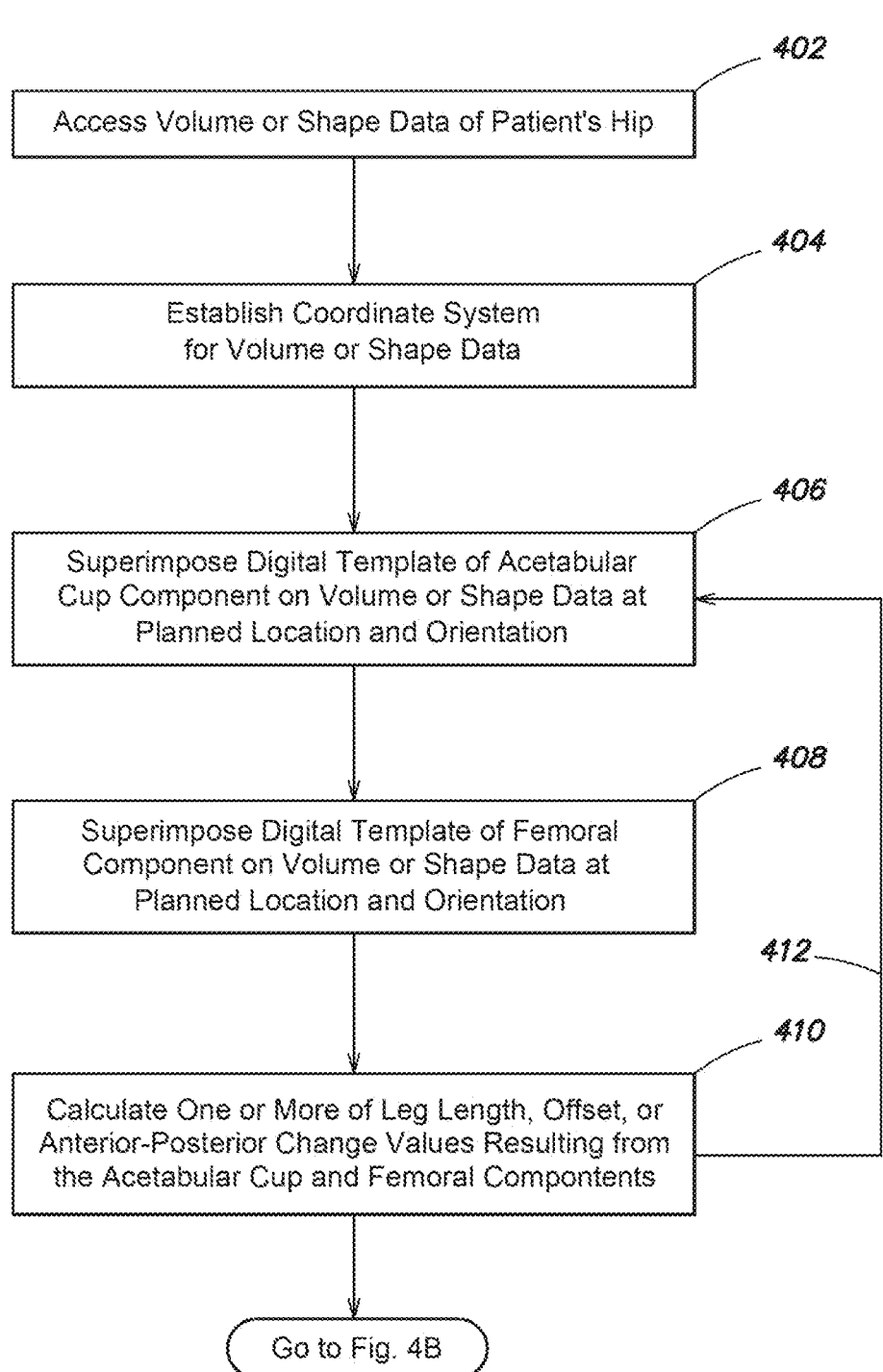

*402*
Access Volume or Shape Data of Patient's Hip

*404*
Establish Coordinate System
for Volume or Shape Data

*406*
Superimpose Digital Template of Acetabular
Cup Component on Volume or Shape Data at
Planned Location and Orientation

*408*
Superimpose Digital Template of Femoral
Component on Volume or Shape Data at
Planned Location and Orientation

*412*

*410*
Calculate One or More of Leg Length, Offset, or
Anterior-Posterior Change Values Resulting from
the Acetabular Cup and Femoral Compontents Go to Fig. 4B

*FIG. 4A*

CUP:
OD=58  *642*
ID=36

STEM:
Type=12
Neck=127° Long
H-LEN=L

LL/OFSET:
LL=+5.4mm
Offset=−2.8mm  *646* *648*

NAT FEM:
AnteV=11.4°  *650*

PLAN FEM:
AnteV=13.3°  *652*
*644*

DIST:
TipGT-Impl=31.6mm  *654*
TipLT-Impl-5.2mm  *656*

SYSTEMS AND METHODS FOR DETERMINING LEG LENGTH CHANGE DURING HIP SURGERY

CROSS-REFERENCE TO RELATED APPLICATIONS

The present application is a continuation of U.S. patent application Ser. No. 17/475,953 filed Sep. 15, 2021, which is a continuation of U.S. patent application Ser. No. 15/918, 696 filed Mar. 12, 2018, now U.S. Pat. No. 11,147,626, which claims the benefit of U.S. Provisional Patent Application Ser. No. 62/471,049 filed Mar. 14, 2017 by Stephen B. Murphy and William S. Murphy for SYSTEMS AND METHODS FOR DETERMINING LEG LENGTH CHANGE DURING HIP SURGERY, which applications are hereby incorporated by reference in their entireties.

BRIEF DESCRIPTION OF THE DRA WINGS

The description below refers to the accompanying drawings, of which:

FIGS. 4A and 4B are partial views of a flow diagram of an example method in accordance with one or more embodiments;

Figure 8A:
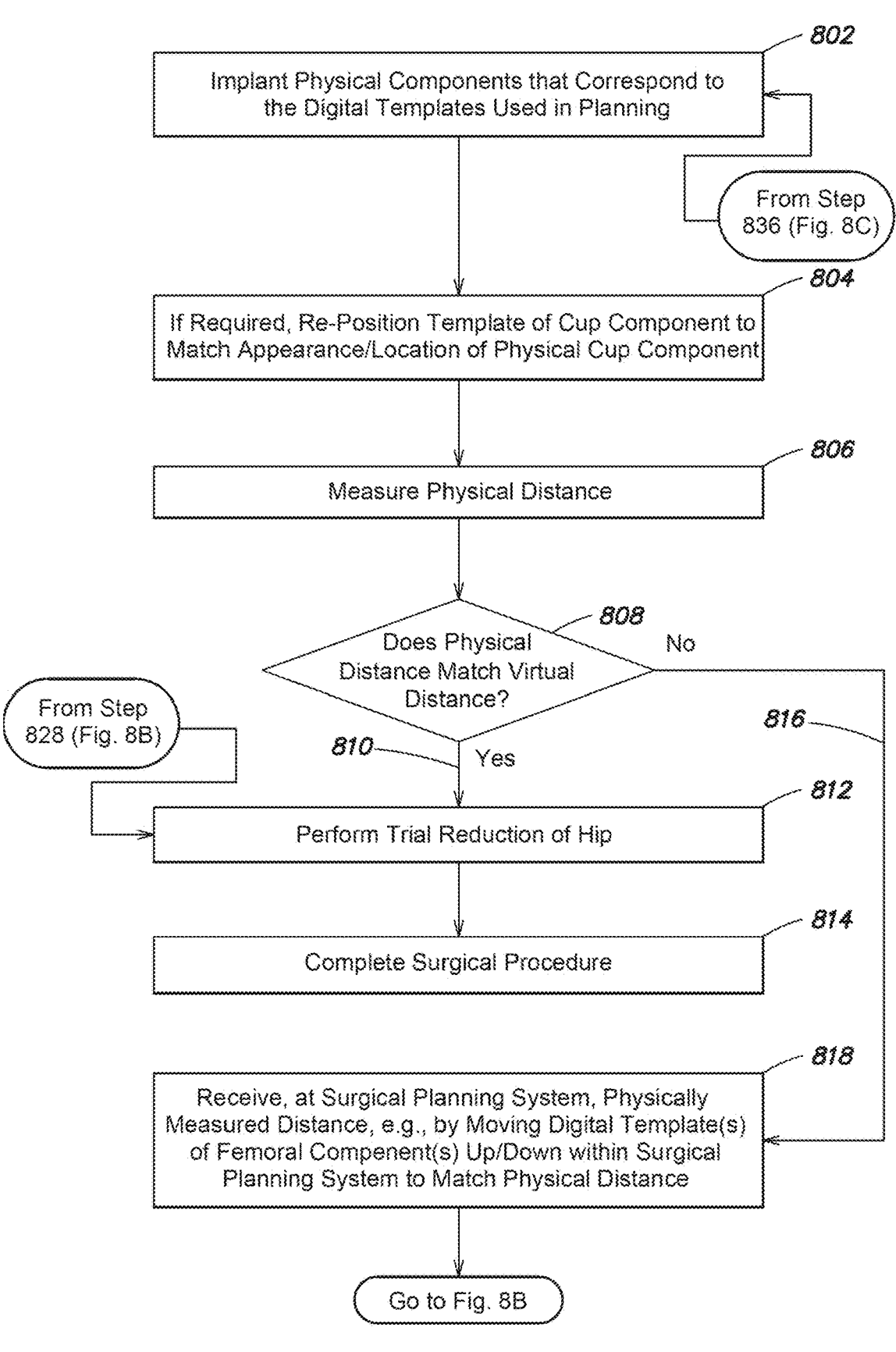
Figure 8B:
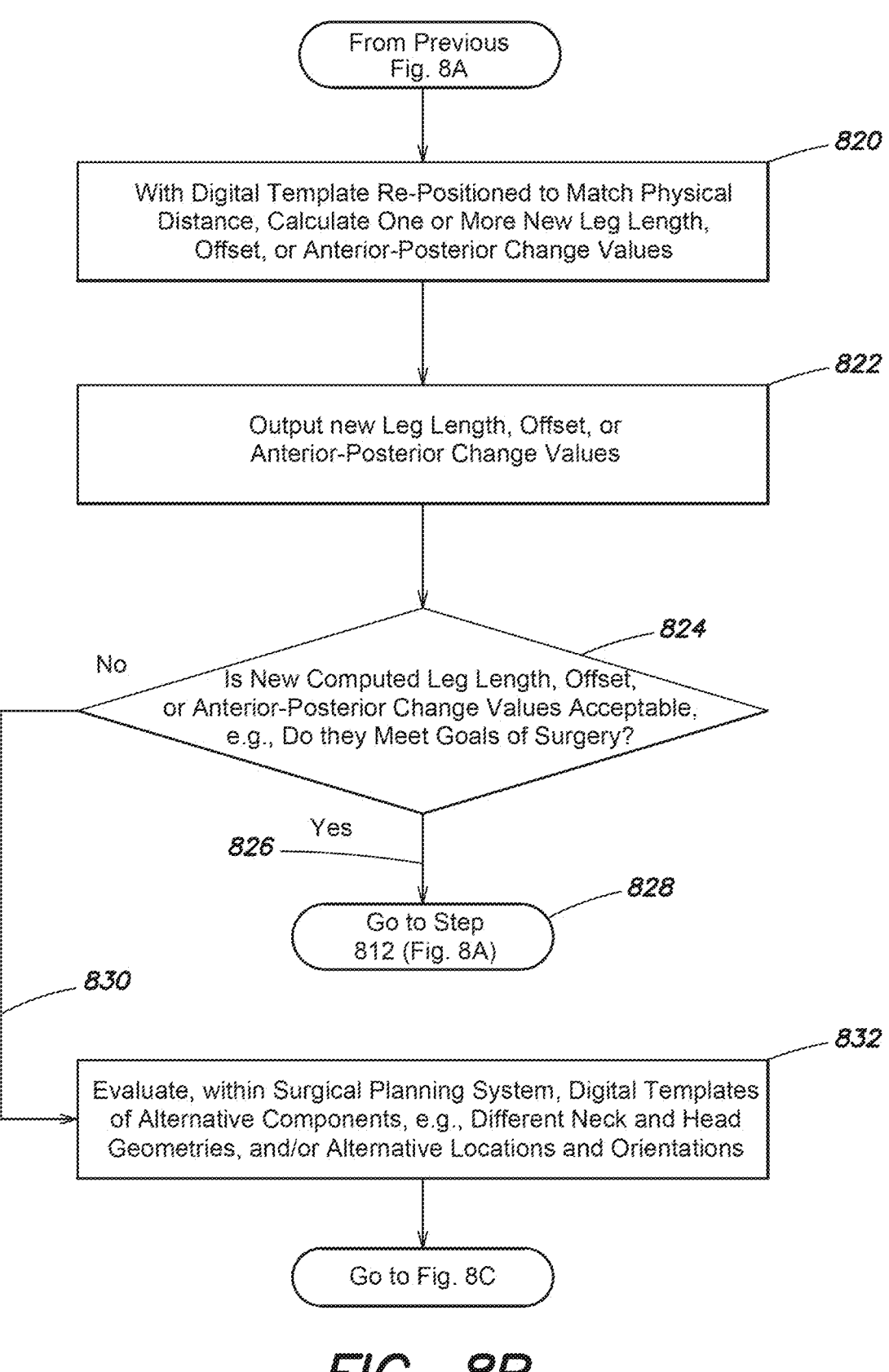
Figure 8C:
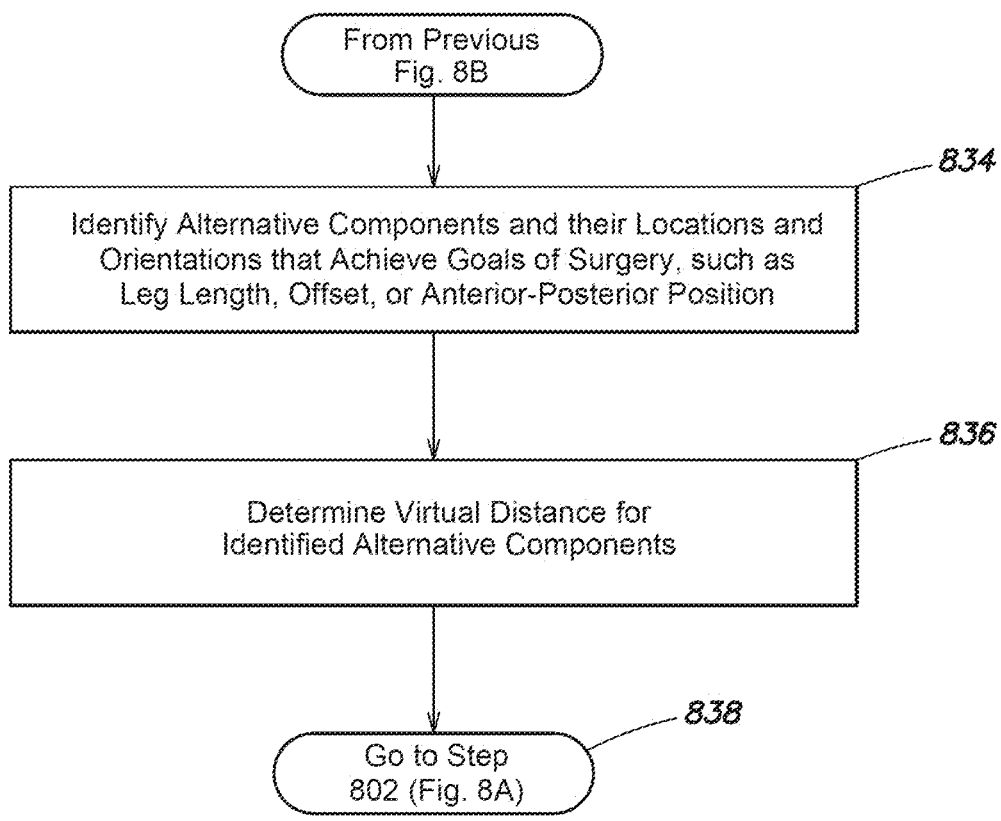
Figure 9A:
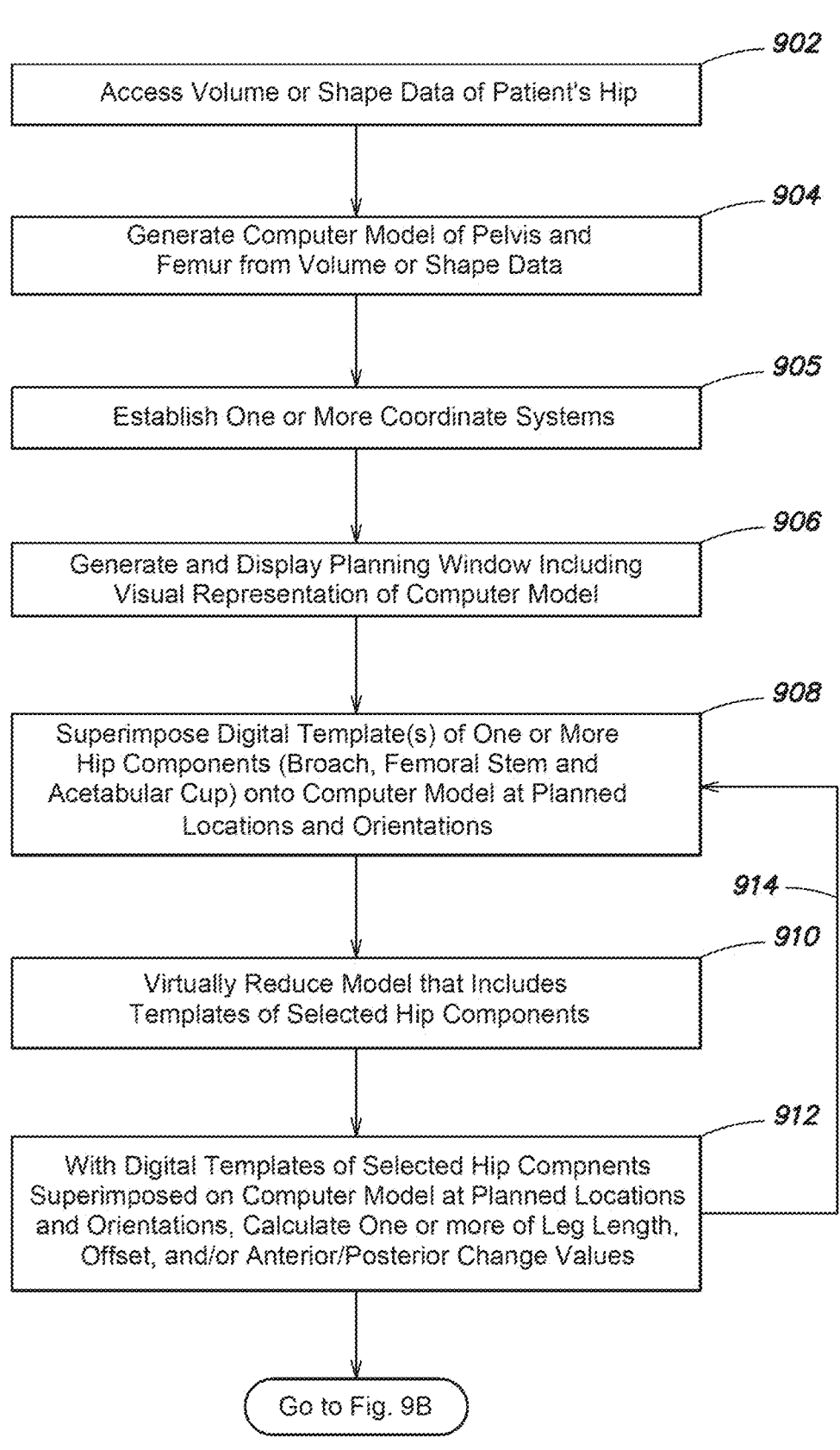
Figure 9B:
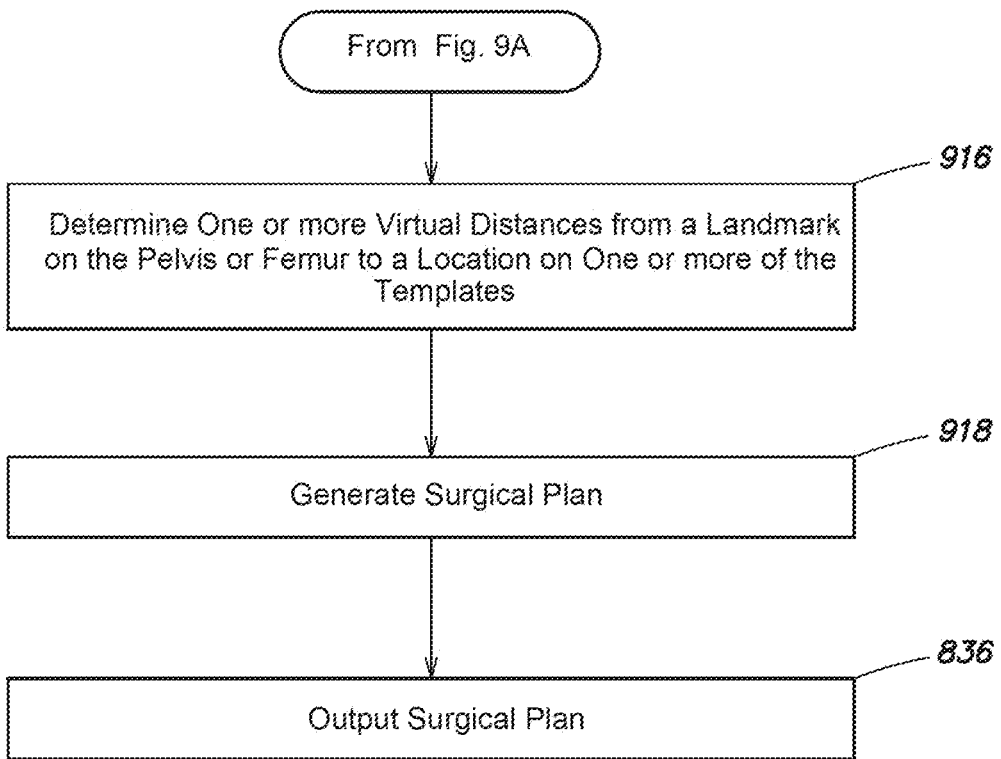
Figure 10:
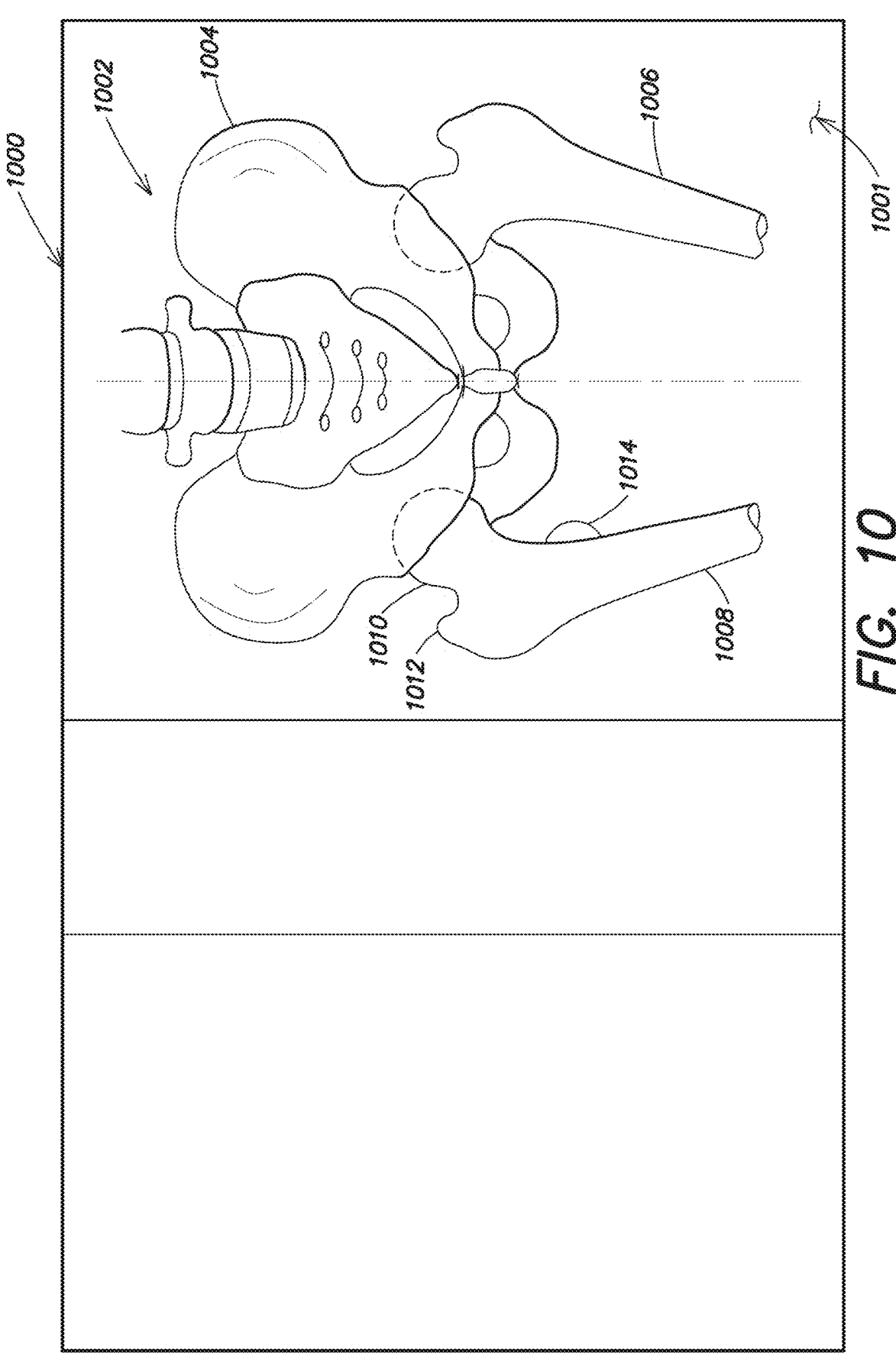
Figure 11:
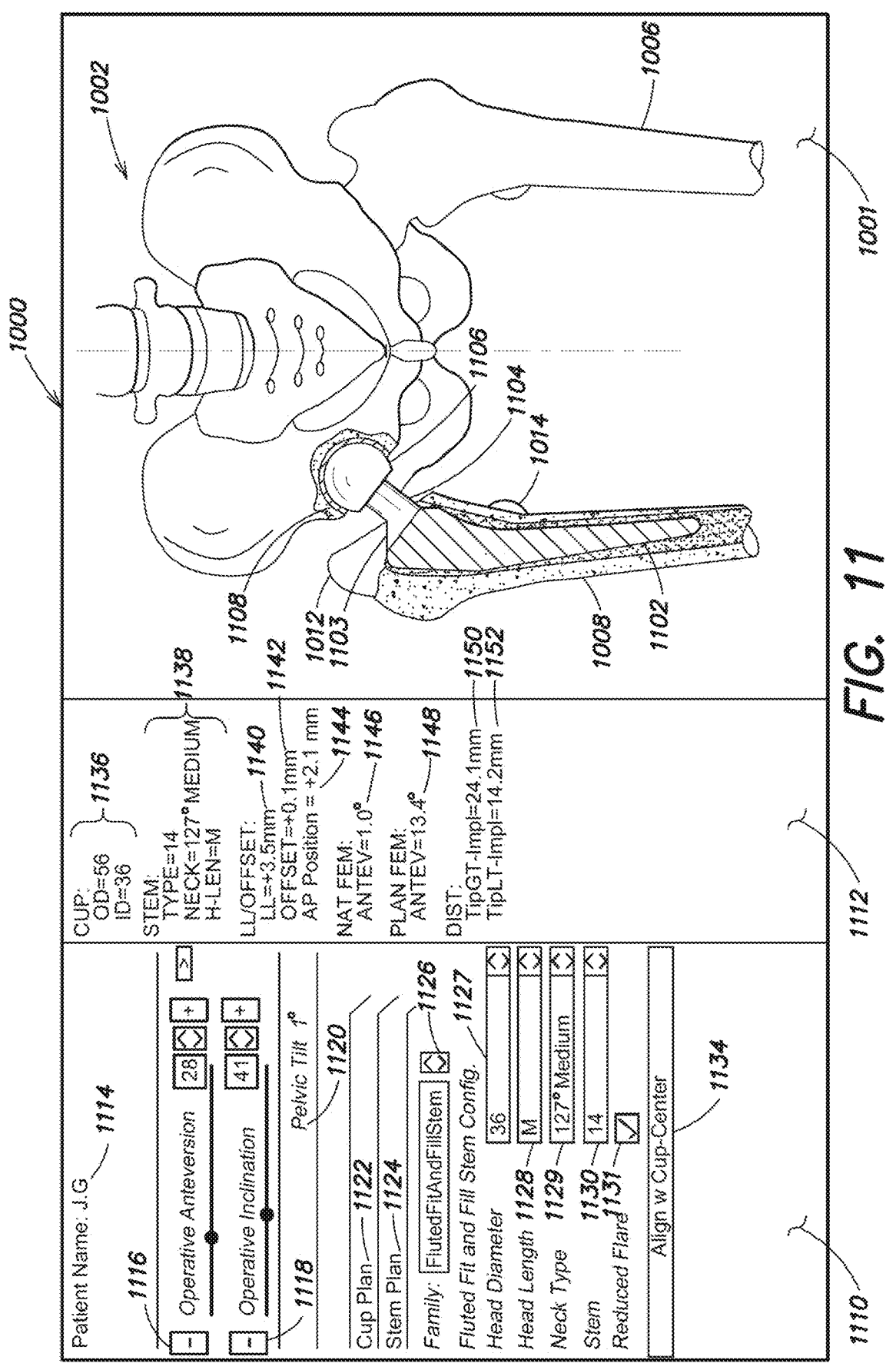
Figure 12:
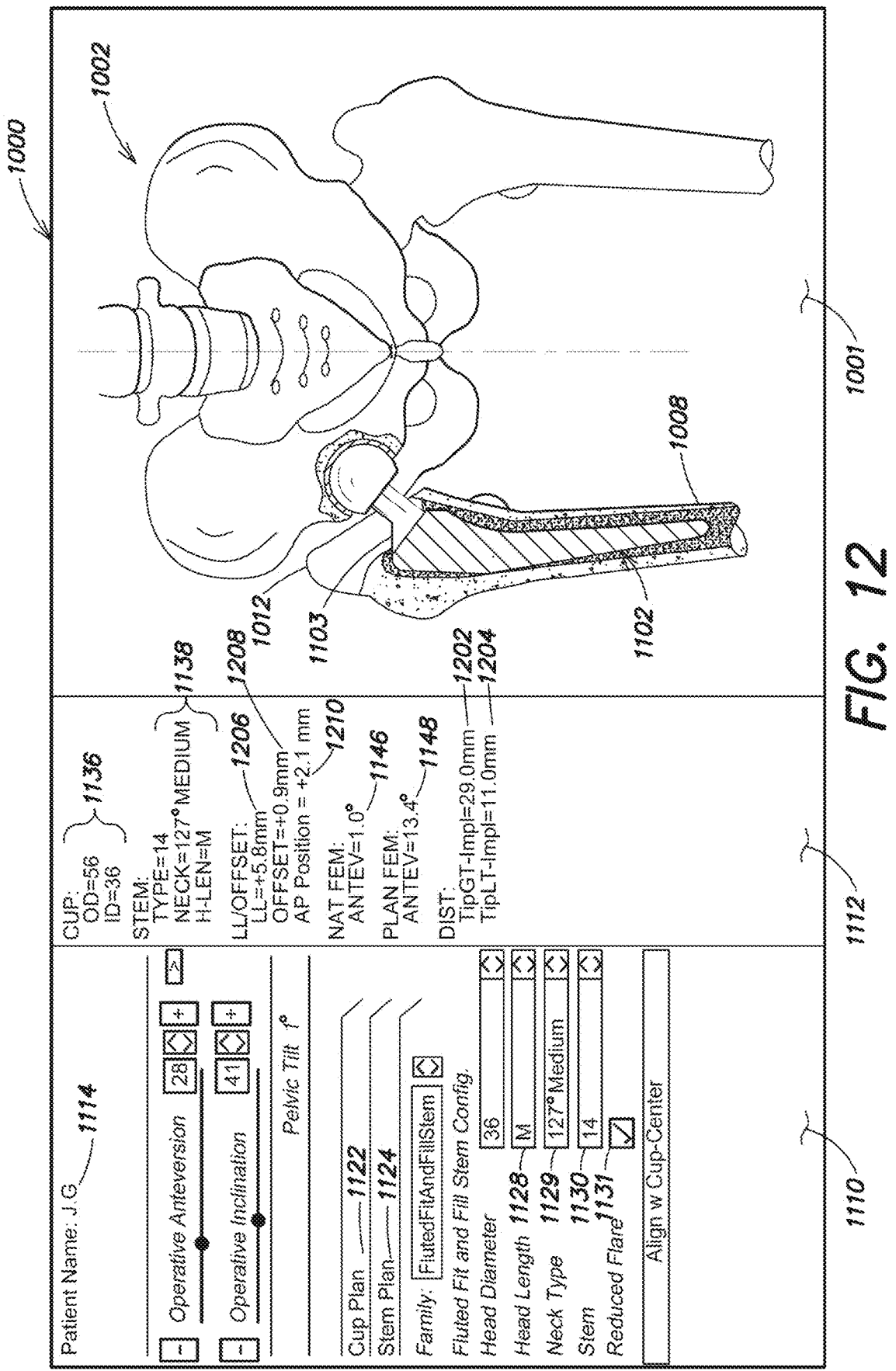
Figure 13:
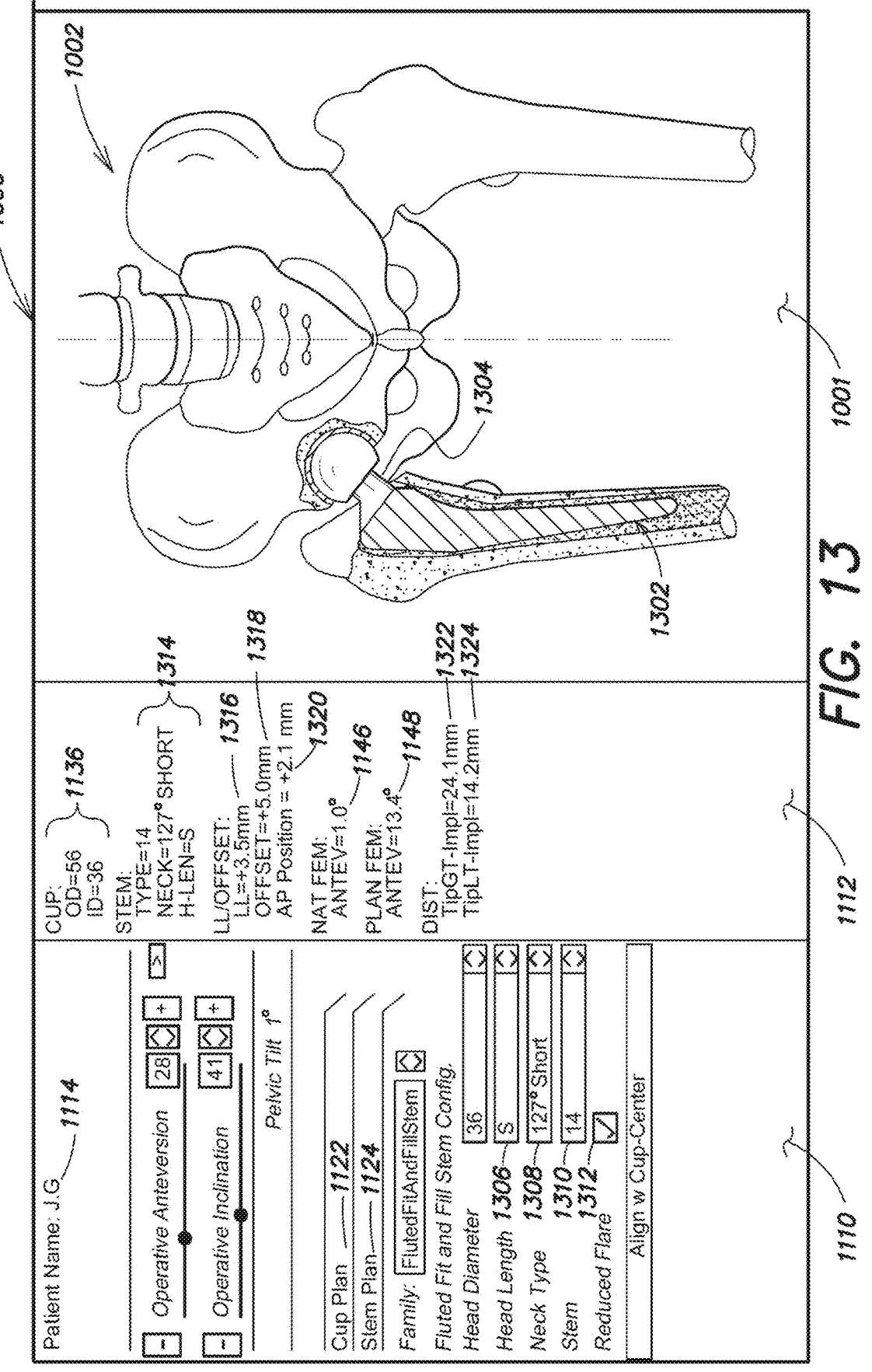
Figure 14:
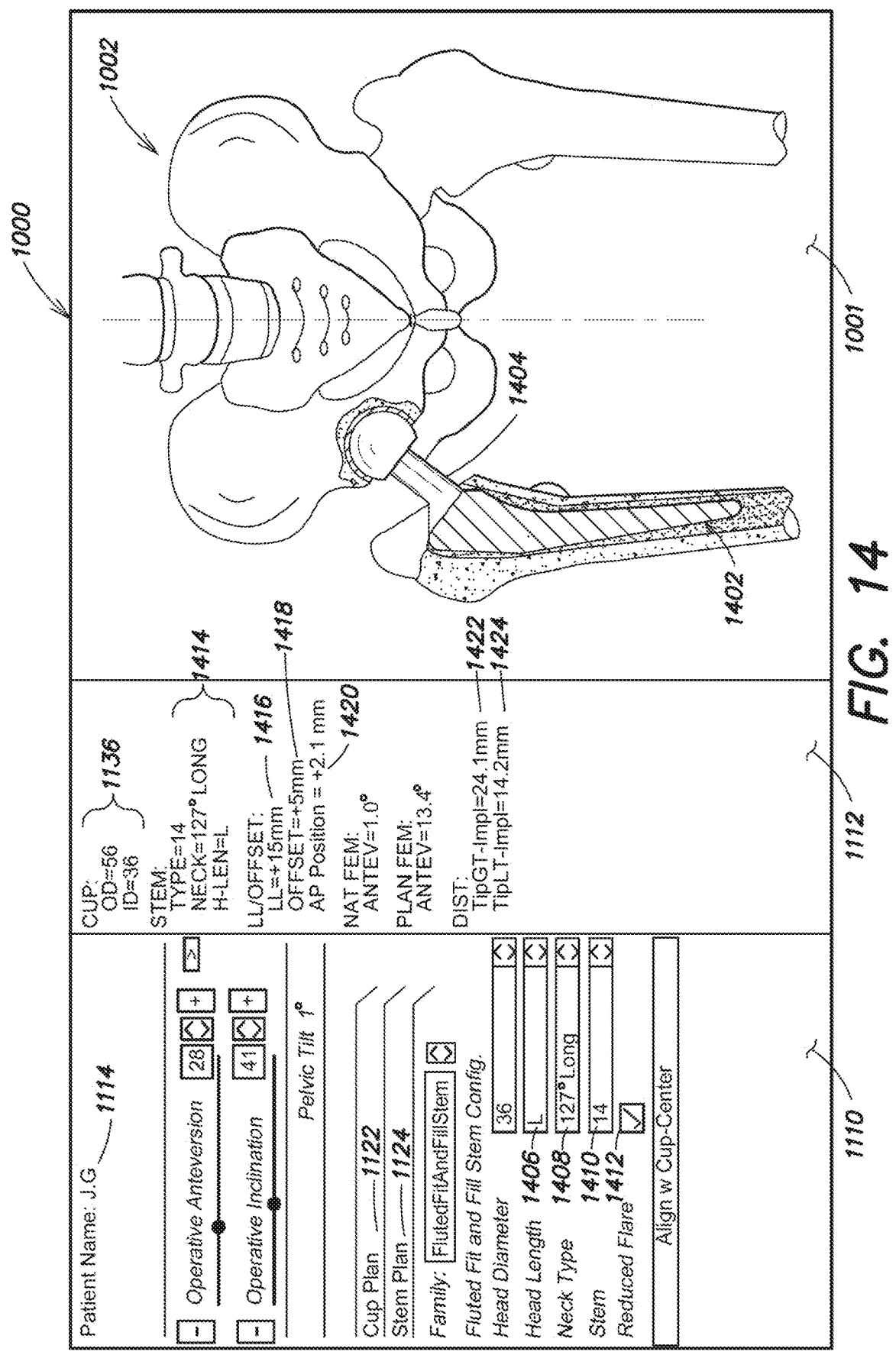
Figure 15:
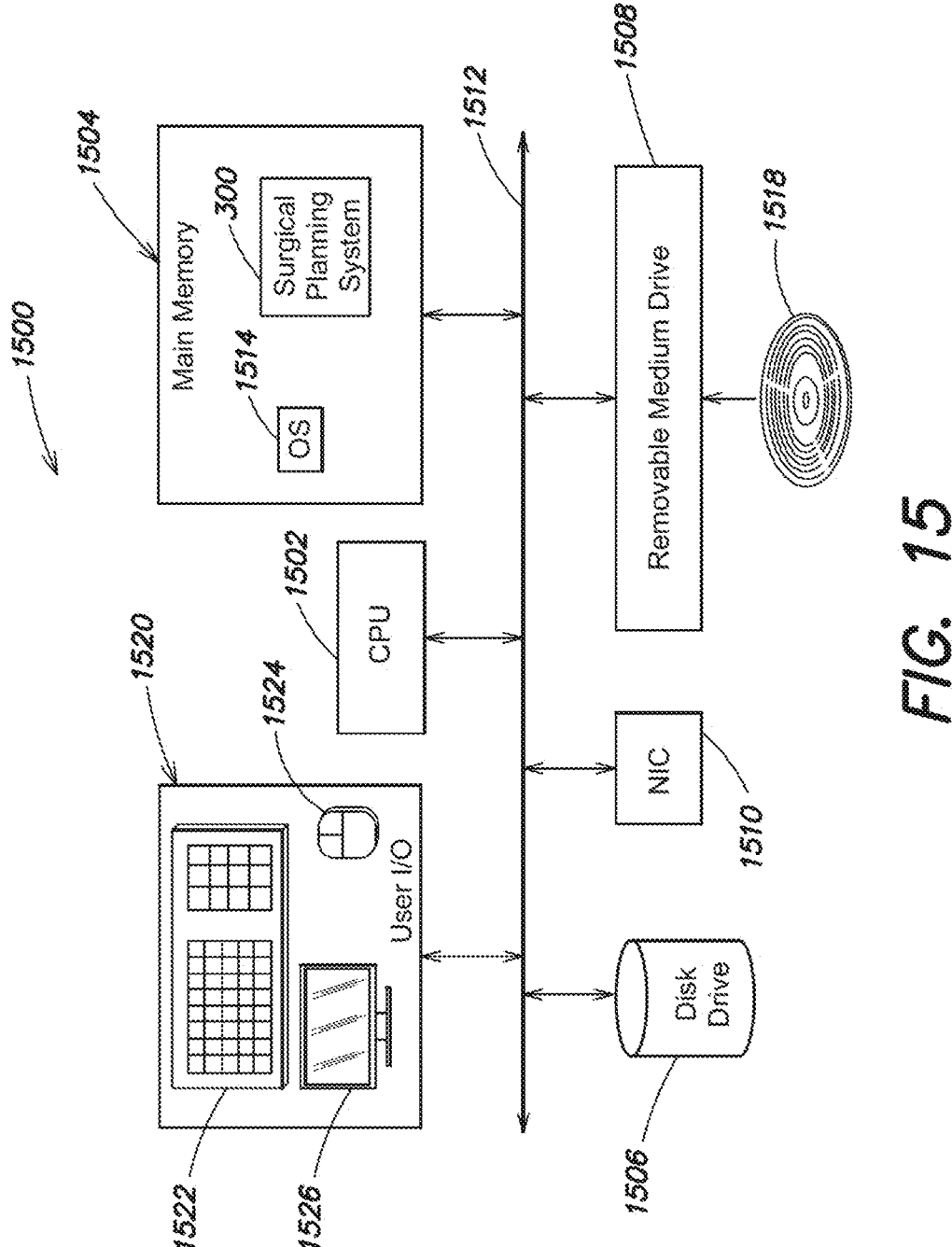
Figure 16:
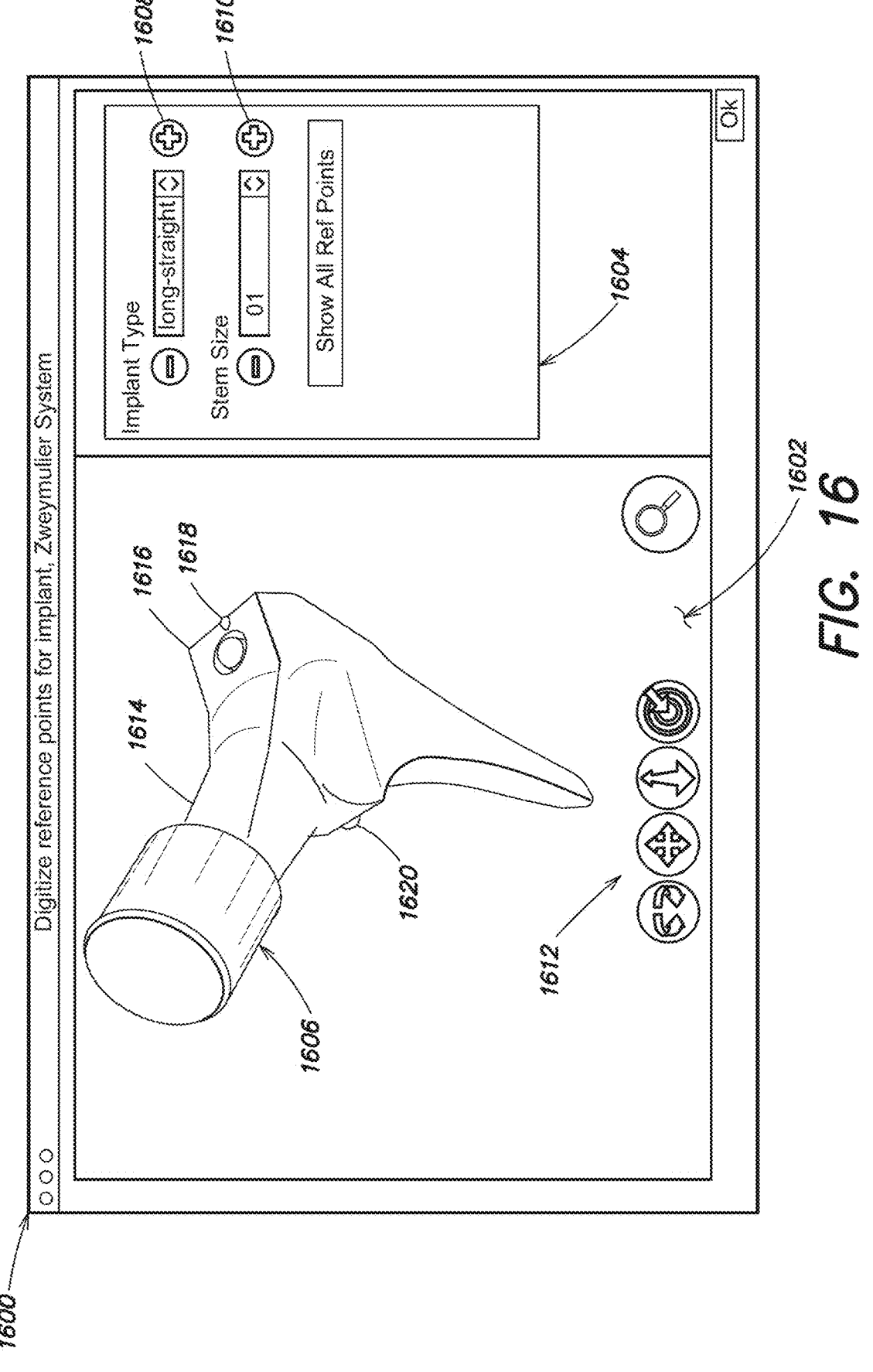

FIGS. 8A-C are partial views of a flow diagram of an example method in accordance with one or more embodiments;

FIGS. 9A and 9B are partial views of a flow diagram of an example method in accordance with one or more embodiments;

FIG. 10 is a schematic illustration of an example planning window in accordance with one or more embodiments;

FIG. 11 is a schematic illustration of the example planning window of FIG. 10 including digital templates of hip components in accordance with one or more embodiments;

FIG. 12 is a schematic illustration of an example planning window in accordance with one or more embodiments;

FIG. 13 is a schematic illustration of an example planning window in accordance with one or more embodiments;

FIG. 14 is a schematic illustration of an example planning window in accordance with one or more embodiments;

FIG. 15 is a schematic illustration of an example data processing device in accordance with one or more embodiments; and FIG. 16 is a schematic illustration of an example CAD drawing of an implant presenting in a modeling window in accordance with one or more embodiments.

DETAILED DESCRIPTION OF ILLUSTRATIVE EMBODIMENTS

Figure 1:
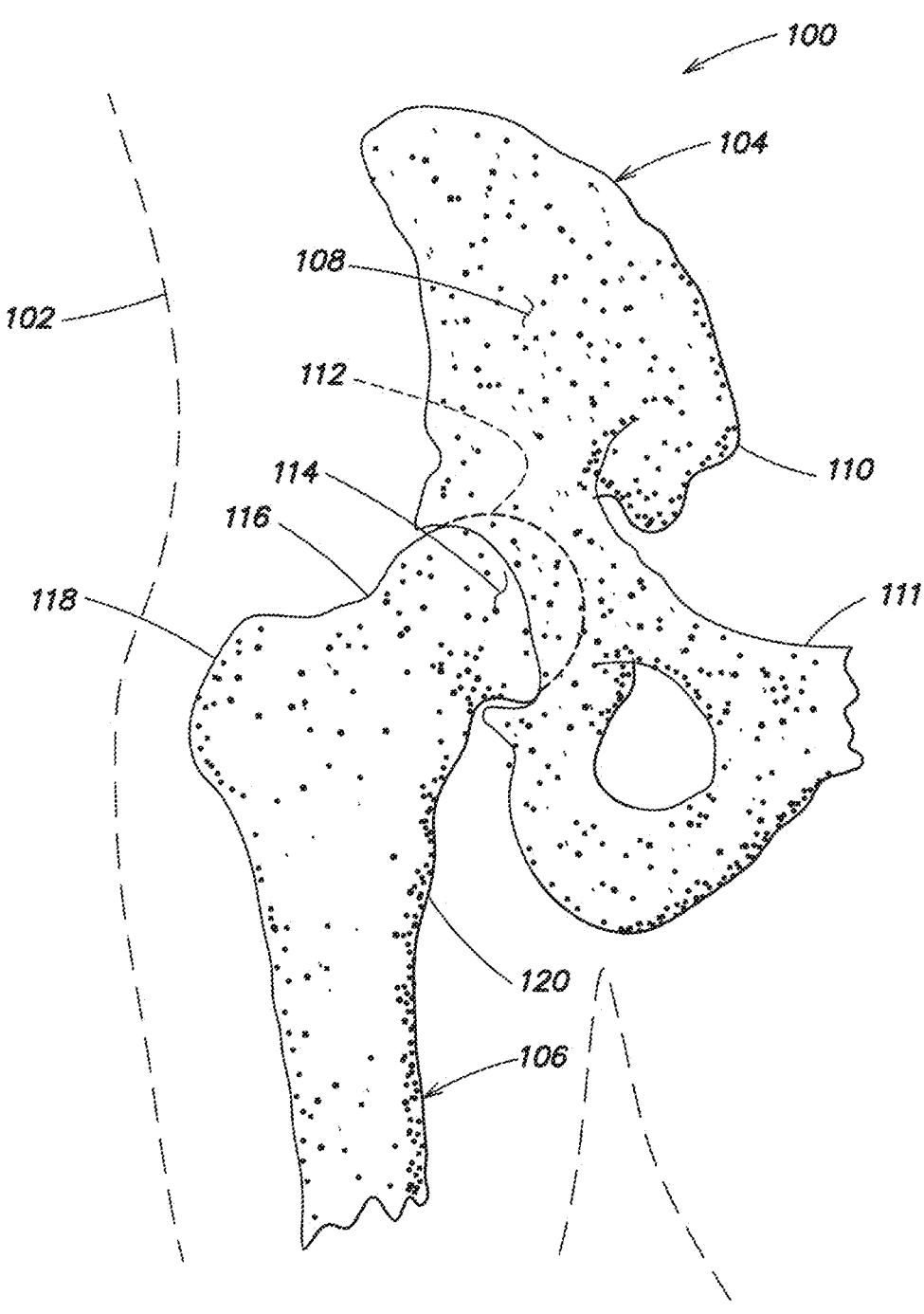
FIG. 1 is a schematic illustration of a portion of a human hip.

Human hip joints can suffer deterioration, for example, due to aging, deformity, illness, or injury. Orthopedic prosthetic implants are commonly used to replace some or all of a hip joint in order to restore its use, resulting from such deterioration. FIG. 1 is a schematic illustration of a portion of a hip 100 of a patient 102. The hip 100 includes a pelvis 104 and a femur 106. The pelvis 104 includes an ilium 108, an anterior superior iliac spine (ASIS) 110, a pubis 111, and an acetabulum 112. The femur 106 includes a head 114, a neck 116, a greater trochanter 118, and a lesser trochanter 120.

In total hip replacement or total hip arthroplasty, a portion of the patient's native femur including the femoral head and a portion of the femoral neck is resected and replaced with a prosthetic femoral component. The femoral component typically includes a femoral hip stem including a neck portion and a femoral head. A portion of the femoral hip stem is positioned within a femoral canal of the patient's femur. The femoral hip stem may be secured within the canal using bone cement, or through ingrowth of surrounding bone into the stem. The neck portion extends from a proximal end of the femoral hip stem, and supports the prosthetic femoral head. The prosthetic femoral head is received within a prosthetic acetabular component, such as an acetabular cup inserted into the patient's acetabulum. An acetabular liner may be placed inside the acetabular cup.

The prosthetic hip joint components may be modular components. For example, the femoral hip stem, the neck portion, and the femoral head may be separate components. In some embodiments, the neck portion and/or a proximal body portion may be formed from modular components. Because they are modular, components having different sizes or different design characteristics may be selected to form a particular implant.

Figure 2:
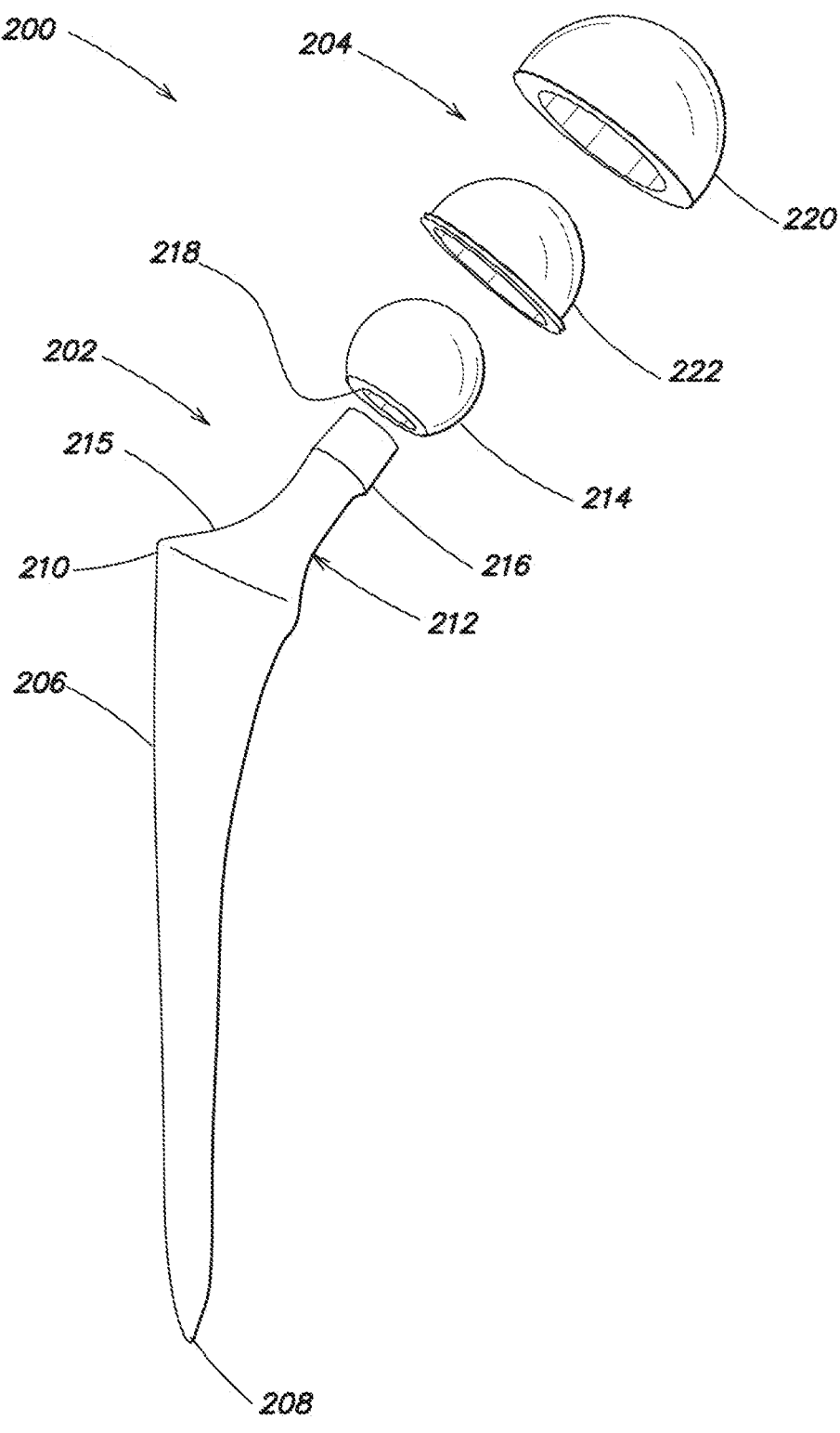
FIG. 2 is an exploded view of an example of a modular hip implant in accordance with one or more embodiments.

FIG. 2 is an exploded view of an example modular hip implant 200 in accordance with an embodiment. The hip implant 200 may include a femoral assembly 202 and an acetabular assembly 204. The femoral assembly 202 may include an elongated femoral hip stem 206 having a distal end 208 and a proximal end 210. The femoral assembly 202 may further include a prosthetic neck portion 212 and a prosthetic femoral head 214. The neck portion 212 may be attached to the proximal end 210 of the femoral hip stem 206. The neck portion 212 may include a shoulder 215 and a mount 216. The femoral head 214 may include a bore 218, allowing the femoral head 214 to be attached to the neck portion 212 and thus to the femoral hip stem 206, for example by receiving the mount 216 within the bore 218. The acetabular assembly 204 may include an acetabular cup 220 and a liner 222 that fits within the acetabular cup 220.

It should be understood that the example hip implant 200 is meant for illustrative purposes only, and that the present disclosure may be used with hip implants of other designs including hip implants with additional or fewer modular components or elements. For example, a hip implant may include a hip stem with an integrated neck portion where the hip stem and neck portion are a single, unitary component. Such stems may be available in different neck length and neck angle combinations, such as short and long neck lengths, and 127° and 135° neck angles. Alternatively, fixed necks may come with standard offset and high offset versions where the high offset may result in the head center being 8 mm further from the longitudinal stem axis as compared to the standard offset version, with the longitudinal location of the head center being unchanged.

Exemplary hip implants include the Synergy hip system from Smith & Nephew, Inc. of Memphis, Tennessee, the Summit hip system available from Depuy Orthopaedic, Inc. of Warsaw, Indiana, and the Epoc Hip System available from Biomet, Inc. of Warsaw, Indiana, among others. The present invention also may be used with non-modular hip implants.

When a hip joint is replaced, changes in leg length, offset, and/or anterior-posterior (AP) position may occur. Leg length refers to the longitudinal extent of the leg, and may be measured, e.g., from a location on the pelvis down to some location along the leg, such as a point on the femur. Offset refers to the lateral or transverse dimension through the hip. The AP position refers to changes along an axis orthogonal to the longitudinal and lateral or transverse axes. Large changes in leg length, offset, and/or AP position as a result of hip replacement surgery can be desirable or undesirable. For example, if the leg of a hip being operated on is 10 mm shorter than the patient's other leg, e.g., due to hip pathology, it may be desirable to reconstruct the hip with 10 mm of additional length. Conversely, if a patient's legs are of equal length before surgery, and the leg of the hip being operated on is lengthened, such that it is 10 mm longer, such an outcome may be undesirable. Similarly, leaving the leg of a hip being operated on short, and the hip with soft tissue laxity can result in an unstable hip joint, potentially leading to repeated hip dislocations and the need for revision, i.e., corrective surgery. Unequal leg lengths can also lead to trunk imbalance, excessively tight tissues, and discomfort.

A surgeon may choose particular hip components, and may plan their position within the hip in order to accomplish a particular goal for the surgery, such as optimizing the changes in leg length, offset, and/or AP position for the patient. In some cases, optimizing the changes may mean minimizing changes to leg length, offset, and/or AP position. In other cases, it may mean achieving particular changes to leg length, offset, and/or AP position. To achieve the goals set for the hip replacement surgery, a surgeon may select particular femoral and acetabular components prior to the surgical procedure, e.g., during a planning stage. The surgeon may also pre-operatively plan the locations and/or orientations of the selected components within the pelvis. The particular components and their locations and orientations may be selected based on patient-specific data, such as patient anatomy. For example, a set of templates of hip joint components may be available to the surgeon. The set of templates may provide two-dimensional (2D) silhouettes of the different sizes and/or shapes of modular components available during surgery. During the planning stage, the surgeon may overlay these 2D templates onto a 2D radiograph of the patient's hip to determine which templates, and thus which components, best fit the patient and/or achieve the goals set for the procedure.

With the advent of digital radiographs, digital templates of modular hip components are now available, and may be used with planning software tools, such as the Ortho View software product from Ortho View Holdings Ltd. of Southampton, Hampshire UK. In some cases, the surgeon may have three-dimensional (3D) patient-specific imaging, and 3D templates of implants may be used during the planning stage. For example, templates in the form Computer Aided Design (CAD) files for respective hip components may be available. Exemplary systems that utilize digital templates include the TraumaCad pre-operative planning system from Brainlab Ltd. of Petach-Tikva, Israel (a division of Brainlab AG of Munich, Germany), and the MAKOplasty Total Hip Application pre-operative and intra-operative planning system from Mako Surgical Corp., Ft. Lauderdale, FL.

During the surgical procedure, the selected components may be implanted at actual locations and orientations, and their effects on the patient's hip evaluated. For example, a trial hip stem component may be placed in the femur, a trial femoral head attached to the stem, and a trial acetabular cup and liner may be inserted into the acetabulum. The trial femoral head may then be inserted into the acetabular cup in a trial reduction of the hip. Leg length, offset, and AP position, and the hip's free range of motion and stability may be assessed to determine if the goals set for the surgery are met. If so, the trial components may be replaced with final components matching the trial components.

If the trial components do not achieve the desired goals, the surgeon may evaluate other components. For example, the surgeon may implant different components, and evaluate these new trial components. This process is time-consuming, and may fail to achieve the best choice of components for the patient.

Briefly, the present disclosure relates to systems and methods for planning and performing hip surgery. The systems and methods may include a User Interface (UI) engine that may generate a Graphical User Interface (GUI) that displays volume or shape data of a patient's hip. The systems and methods may include a library of digital templates of hip components, such as femoral hip stems with modular or fixed necks of various lengths and angles, necks of various lengths and angles, femoral heads, acetabular cups, acetabular cup inserts with various centers of rotation, etc. The systems and methods may include a planning tool, which may be utilized to select particular digital templates from the library and to place, e.g., superimpose, them on the volume or shape data. The digital templates may be two or three-dimensional (2D or 3D). The planning tool may compute change values for leg length, offset, and/or anterior-posterior (AP) position based on the positioning of the templates and their geometries. With the templates placed on the volume or shape data at desired locations and orientations, the planning tool may also compute one or more virtual distances. For example, the planning tool may calculate a virtual distance between one or more landmarks on the volume or shape data and one or more locations on a template. The virtual distance may be a landmark depth, e.g., the depth of a point on a template, such as the shoulder of a femoral stem, from a landmark, such as the greater trochanter. The systems and methods may include the computed change values and virtual distances in an electronic surgical plan. The surgical plan may be an electronic plan that may be opened and viewed in an application program, such as the planning tool, during the surgical procedure on the patient.

During surgery, physical hip components that correspond to the planned components may be implanted at the patient's hip. A physical distance that corresponds to the virtual distance may be obtained and compared to the virtual distance. If the obtained physical distance differs from the virtual distance, the obtained physical distance may be entered in the electronic surgical plan. For example, a template of a component, such as a femoral hip stem, may be repositioned in the plan relative to the volume or shape data so that the position of the template matches the physical distance obtained during surgery. With the template repositioned to match the obtained physical distance, the systems and methods may automatically calculate and present new changes in leg length, offset, and/or AP position based on the now repositioned template. The new changes may be evaluated by the surgeon, and a determination may be made whether they meet the goals set for the procedure. In addition, with the template repositioned to match the obtained physical distance, the systems and methods can evaluate the effects on leg length, offset, and/or AP position of other hip joint components by substituting new templates into the plan. For example, the surgeon may substitute the existing templates for templates representing different hip joint components, such as other neck angles, neck lengths, and/or head lengths. The systems and methods may dynamically and automatically calculate new changes in leg length, offset, and/or AP position based on the positioning and the geometry of the new templates. The systems and methods may present these new change values to the surgeon in one or more user interfaces for evaluation.

In other words, the systems and methods may establish a dynamic design and evaluation feedback loop that may be utilized during the surgical procedure to optimize the selection, position, and orientation of hip components for the patient, based on the actual location and orientation of one or more hip components. For example, if the planned hip components do not achieve the goals set for the surgical procedure after being repositioned to match the obtained physical distance, templates for different hip joint components may be selected and evaluated, through the electronic surgical plan. In particular, the systems and methods may compute new change values for leg length, offset, and/or AP position using templates for different hip joint components selected by the surgeon. For example, the surgeon may select and evaluate a template representing a smaller stem component that may go in further to the femur, a larger stem that may sit up higher on the femur, and/or available combinations of neck angles and neck lengths and head lengths and diameters. This process of choosing templates for different hip joint components and calculating the resulting changes in leg length, offset, and/or AP position may be repeated or continued until a set of hip joint components is found that achieves the goals set for the surgical procedure. In some embodiments, new virtual distances also may be computed, and templates may be repositioned to match obtained physical distances. The dynamic design and evaluation feedback loop may be utilized prior to any trial reduction of the patient's hip.

Once the dynamic design and evaluation feedback loop narrows the selection down to a final set of hip joint components, physical components corresponding to the final set may be implanted at the patient's hip.

In some embodiments, physical distances for one or more of the final set of hip joint components may be obtained and entered in the system, and the systems and methods may again compute leg length, offset, and/or AP position change values based on the obtained physical distances. If the new change values meet the goals set for the procedure, the surgeon may proceed with the surgical procedure. For example, a trial reduction may be performed, and the hip evaluated. The surgical procedure may then be completed. Alternatively, the process of evaluating alternative components and/or locations and orientations in the electronic surgical plan may be repeated until leg length, offset, and/or AP position change values are obtained that meet the goals set for the procedure.

Figure 3:
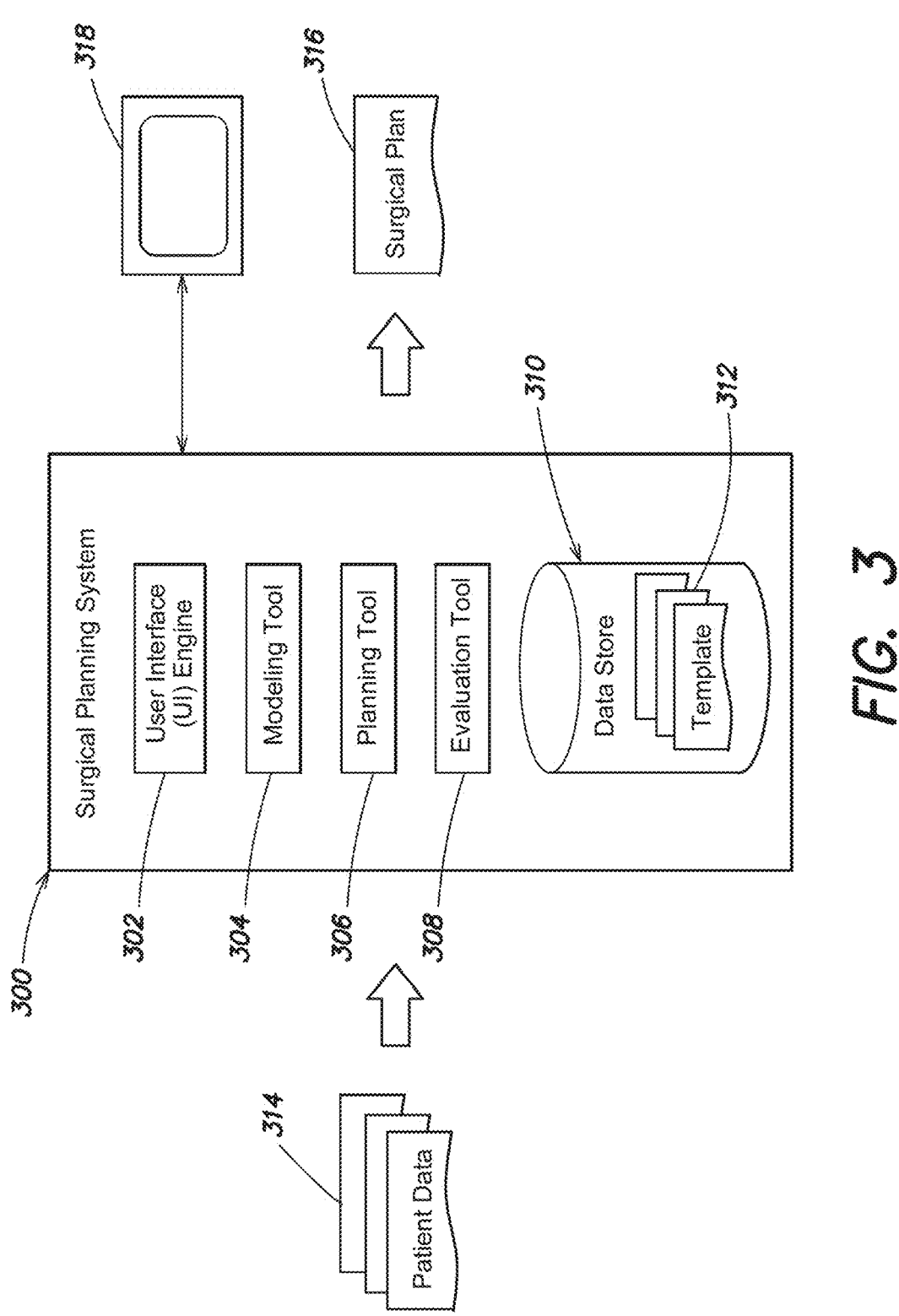
FIG. 3 is a schematic illustration of an example surgical planning system in accordance with one or more embodiments.

FIG. 3 is a schematic illustration of an example surgical planning system 300 in accordance with an embodiment. The surgical planning system 300 may include a user interface (UI) engine 302, a modeling tool 304, a planning tool 306, an evaluation tool 308, and a data store 310. The data store 310 may include digital templates of hip joint components, as indicated at 312. The surgical planning system 300 may receive patient data, as indicated at 314, which may include volume or shape data in the form of magnetic resonance imaging (MRI) data, computed tomography (CT) data, simultaneous biplanar radiography data, conventional plain radiograph data, ultrasonic data, and/or other data of a patient's hip. The surgical planning system 300 may create one or more electronic surgical plans, such as plan 316, for the hip surgery. The surgical planning system 300 may include or have access to a display 318.

Suitable tools for generating 2D and/or 3D displays of anatomical structures from volume or shape data include the OsiriX image processing software from Pixmeo SARL of Bernex Switzerland, the TraumaCad pre-operative planning system, and the MAKOplasty Total Hip Application pre-operative and intra-operative planning system. Nonetheless, those skilled in the art will understand that other image processing software may be used.

One or more of the UI engine 302, modeling tool 304, planning tool 306, and evaluation tool 308 may be or may include software modules or libraries containing program instructions pertaining to the methods described herein, that may be stored on non-transitory computer readable media, and executed by one or more processors of a data processing device. In some embodiments, one or more of the UI engine 302, modeling tool 304, planning tool 306, and evaluation tool 308 may each comprise registers and combinational logic configured and arranged to produce sequential logic circuits. In other embodiments, various combinations of software and hardware, including firmware, may be utilized to implement the present disclosure.

One or more of the patient data 314, the templates 312, and the surgical plan 316 may be implemented through one or more data structures, such as files, objects, etc., stored in the electronic memory of a data processing device. The templates may represent broaches, femoral hip stems, necks, femoral heads, acetabular cups, liners, etc.

Planning

Figure 4B:
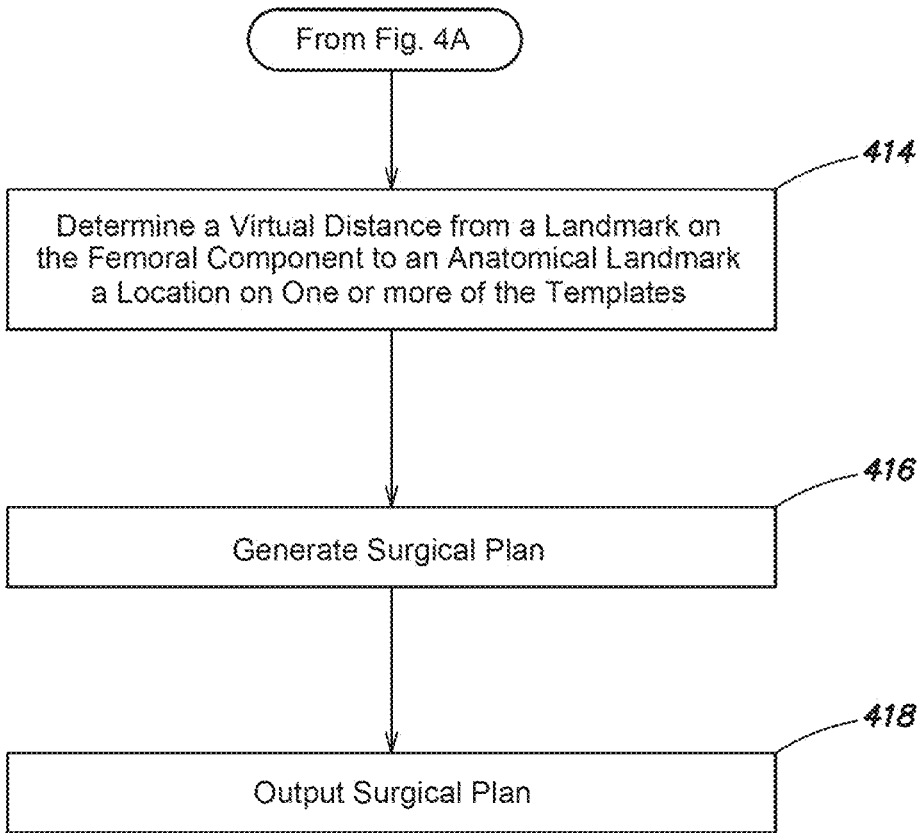

FIGS. 4A-4B are partial views of a flow diagram of an example method in accordance with an embodiment. The surgical planning system 300 may access volume or shape data for a patient's hip, as indicated at step 402. As described, the volume or shape data may be or may be derived from MRI data, CT scan data, biplane simultaneous radiography data, conventional radiography data, ultrasonic data, and/or other imaging data. For example, the patient may undergo MRI, CT, or x-ray studies, and the resulting data may be provided to the system 300. The volume or shape data may be in digital format, such as one or more electronic files or objects.

The surgical planning system 300 may establish one or more coordinate systems for the volume or shape data, as indicated at step 404. In some embodiments, the surgical planning system 300 may establish a pelvic coordinate system and a femoral coordinate system. A suitable pelvic coordinate system is the Anterior-Posterior coordinate system. The femoral coordinate system may include a femoral axis (FA), an axis of the femoral neck (FNA), and a condylar axis (CA). The femoral axis (FA) may be defined to pass through a point (O) at the center of the base of the femoral neck and a point (K) at the center of the knee. The axis of the femoral neck may be defined to pass through the point (O) at the center of the base of the femoral neck and a point at the center of the femoral head (H). The femoral coordinate system may include a condylar plane (CP) and a plane of anteversion (AP). The femoral axis (FA) may lie in both the condylar plane (CP) and the anteversion plane (AP). The anteversion plane (AP) may be at an angle of anteversion ($\theta$) relative to the condylar plane (CP).

In some embodiments, the surgeon may mark a number of points on the volume or shape data as displayed on the GUI. For example, the surgeon may mark:

the point (O) at the center of the base of the femoral neck;
the point (K) at the center of the knee;
the left spina iliaca anterior superior (SIAS);
the right SIAS;
the femur head center;
the lateral condyle;
the media condyle;
the greater trochanter; and
the lesser trochanter.

It should be understood that additional, fewer, or other points may be marked in other embodiments.

In response to user input, the planning tool 306 may superimpose a selected digital template of an acetabular cup component onto the volume or shape data at a selected location and orientation, as indicated at step 406. The planning tool 306 may also superimpose a selected digital template of one or more femoral components onto the volume or shape data at a selected location and orientation in response to user input, as indicated at step 408. The digital templates may be obtained from the data store 310. In particular, a surgeon or other medical practitioner may select digital templates 312 representing particular acetabular and femoral components from the data store 310. In response, the planning tool 306 may superimpose the digital templates onto a display of the volume or shape data. The geometries of the templates may match the geometries of the respective physical components. The planning tool 306 may move the digital templates 312 to desired locations and orientations relative to the display of the volume or shape data, in response to user inputs. For example, the digital templates may be repositioned and/or re-oriented relative to views of the femur and/or the acetabulum as presented on a display.

The evaluation tool 308 may calculate changes in leg length, offset, and/or AP position due to changes in the hip joint resulting from the placement of the templates for the selected hip joint components, as indicated at step 410. The changes in leg length, offset, and/or AP position may be determined relative to the established coordinate system, e.g., the femoral coordinate system, the pelvic coordinate system, or both. The evaluation tool 308 may utilize the geometry of the hip joint components as reflected in the templates when computing changes in leg length, offset, and/or AP position.

In some embodiments, the evaluation tool 308 may determine acetabular contributions to leg length and offset and femoral contributions to leg length and offset. Acetabular contributions may be determined in a pelvic coordinate system, such as the anterior pelvic plane coordinate system, which may correct for unusual positioning of the patient's pelvis on a CT scanner, for example due to severe scoliosis of the spine or spontaneous fusion or severe contracture of the hip. In other embodiments, a functional coordinate system may be established, which may correspond to a raw CT coordinate system with the patient's pelvis in a supine position, for example with the patient lying in the CT gantry.

Femoral contributions to leg length may be computed in a femoral coordinate system, where longitudinal changes can be measured, for example along an axis defined between the center of the native femoral head and the center of the knee or along the axis of the center of the femoral shaft itself. Femoral contributions to offset may be computed in a condylar plane.

Leg length change may be computed by summing the acetabular and femoral leg length contributions. Offset change may be computed by summing the acetabular and femoral offset contributions. For example, the evaluation tool 308 may determine a center of rotation of the patient's native femoral head in the patient's acetabulum, using the volume or shape data. The evaluation tool 308 may calculate the acetabular contribution to leg length and offset as the difference between the pre-operative designated hip joint center, e.g., center of the native femoral head, and the reconstructed acetabular component center as measured horizontally and vertically in the AP plane coordinate system. In other embodiments, the distance may be measured in other coordinate systems. For example, it may be measured in a functional coordinate system, such as the position of the patient's pelvis lying supine or standing. The pre-operative designated hip joint center may be automatically determined by the evaluation tool 308 or it may be entered, for example by the surgeon marking the hip joint center on a view of the shape or volume data as displayed on a user interface, such as a Graphical User Interface (GUI).

The evaluation tool 308 may calculate the femoral contribution to offset by calculating a horizontal distance between a point on the top of the greater trochanter and the pre-operative designated hip joint center in a condylar plane coordinate system. The evaluation tool 308 may rotate the condylar plane coordinate system to be medial/lateral to normalize for patient position during CT studies or a rotation or position contracture due to arthrosis. The evaluation tool 308 may automatically determine the point on the top of the greater trochanter or it may be entered, for example by the surgeon marking the point on a view of the shape or volume data as displayed on the GUI. In addition, the evaluation tool 308 may calculate a horizontal distance between the point on the top of the greater trochanter and the center of the reconstructed femoral head in the condylar plane coordinate system. The evaluation tool 308 may determine a change in magnitude of the two horizontal distances, and this change in magnitude may be the femoral contribution to offset.

The evaluation tool 308 may calculate the femoral contribution to leg length as the longitudinal different between the pre-operative designated hip joint center and the center of the reconstructed femoral head in the femoral coordinate system.

For example, an axis in the femoral coordinate system may extend between the point (O) at the center of the base of the femoral neck and the point (K) at the center of the knee. Femoral contributions to leg length changes may be determined along this or another selected axis. As noted, use of femoral coordinate system and/or this axis may reduce or eliminate the effect of random leg position on the CT scanner or joint contracture that may force the leg into a peculiar position in the raw CT coordinate space. For offset, the femur and pelvis may be reduced by virtually adding the offset change, for example in the medial lateral axis of the medial and lateral femoral condyles, to the acetabular contribution in the medial-lateral axis, for example as defined by a line between the two anterior superior iliac spines.

The evaluation tool 308 may compute AP position change along a dimension of pelvic and femoral coordinate systems that is orthogonal to the dimensions in which leg length and offset are computed. For example, the evaluation tool 308 may compute pelvic and femoral contributions to AP position change along a third dimension of the coordinate systems in a similar manner as leg length and offset.

The evaluation tool 308 may measure, e.g., compute, x,y,z changes on the acetabular side in the pelvic coordinate system and x,y,z changes on the femoral side in the femoral coordinate system. The evaluation tool 308 may then add the x,y,z changes in the pelvic coordinate system to the x,y,z changes in the femoral coordinate system to produce leg length, offset, and AP change values. In some implementations, the x,y,z changes in the pelvic coordinate system may be translated to the femoral coordinate system before being added to the x,y,z changes in the femoral coordinate system. It should be understood that the x,y,z changes in the femoral coordinate system may be added, e.g., following a translation, to the x,y,z changes in the pelvic coordinate system. In some embodiments, the evaluation tool 308 may make these computations without doing a virtual rotation of the femur. In addition, leg length, offset, and AP change values can be computed without reducing, e.g., assembling, the hip joint. The evaluation tool 308 may compute leg length, offset, and AP change position regardless of the position of the patient's leg on the CT scanner.

It should be understood that leg length, offset, and/or AP position may be determined in other ways. For example, with digital templates for the acetabular cup and hip stem positioned relative to the volume or shape data as desired, the evaluation tool 308 may determine the center of the acetabular cup and the center of the femoral head, which will typically have different locations. The evaluation tool 308 may determine the vector between these two centers in a coordinate system, such as the AP Anterior Pelvic Plane coordinate system or the femoral coordinate system. The longitudinal portion of this vector may be the leg length change, the lateral or transverse portion may be the offset change, and the portion orthogonal to these two may be the AP change.

In other embodiments, the evaluation tool 308 may utilize the volume or shape data to determine one or more baseline, e.g., native, values for one or more of leg length, offset, or AP position. For example, the evaluation tool 308 may determine distances between selected points on the pelvis and femur from the volume or shape data. With digital templates of selected hip joint components superimposed on a display of the shape or volume data at the planned locations and orientations, new distances may be determined, and the differences between the new distances and the native distances may be calculated for determining leg length, offset, and/or AP position change values.

In some cases, the process of selecting digital templates, positioning them on a display of the volume or shape data, and computing leg length, offset, and/or AP position change values, may be repeated, as indicated by arrow 412, which loops back from step 410 to step 406. For example, the planning surgeon may conclude that the calculated changes in leg length, offset, and/or AP position based on templates for an initial set of hip joint components do not meet one or more goals set for the procedure. To achieve the one or more goals, the surgeon may evaluate other components by selecting the digital templates for such other components, superimposing the templates on a display of the volume or shape data, and moving them to desired locations and orientations. In other cases, the planning surgeon may evaluate and compare multiple different components and/or locations or orientations. Following this iterative design and evaluation process, the surgeon may settle on a set of particular components to be used during surgery, such as a particular femoral hip stem, a particular neck portion, a particular femoral head, a particular acetabular cup, and a particular acetabular liner.

With the digital templates for the desired hip components superimposed on a display of the volume or shape data in the desired positions and orientations, the evaluation tool 308 also may determine one or more virtual distances, as indicated at step 414 (FIG. 4B). One virtual distance may be between a landmark on a component and a landmark on an anatomical structure of the pelvis or the femur. For example, the evaluation tool 308 may determine a longitudinal distance between the greater trochanter 118 (FIG. 1) and the shoulder 215 (FIG. 2) of the template of the femoral hip stem.

The planning tool 306 may generate one or more surgical plans, such as the surgical plan 316, as indicated at step 416. The surgical plan 316 may include the identity of the particular hip components planned for use in the surgical procedure, as well as their planned location and orientation relative to anatomical structures and/or the one or more coordinate systems. The surgical plan 316 also may include the computed changes in leg length, offset, and/or AP position. The surgical plan 316 may additionally include the one or more computed virtual distances. The surgical planning system 300 may output the one or more surgical plans, as indicated at step 418. For example, the surgical plan may be printed, saved to a memory location of one or more data processing devices, and/or transmitted to a recipient, e.g., by email, text, or facsimile. The pre-operative planning stage may then be complete.

Figure 5:
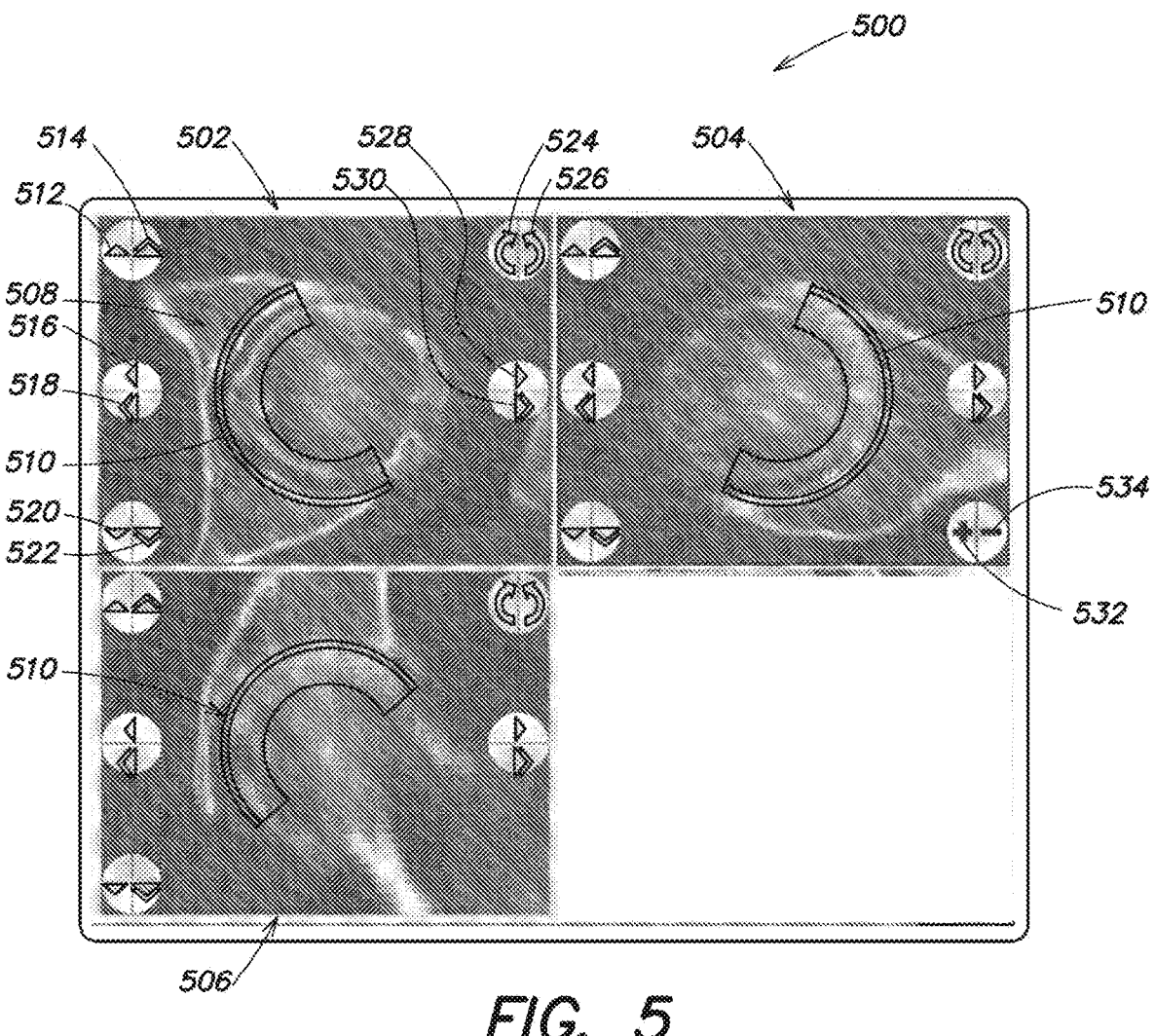
FIG. 5 is a schematic illustration of an example planning window in accordance with one or more embodiments.

FIG. 5 is a schematic illustration of an example planning window 500, which may be generated by the UI engine 302 of the surgical planning system 300, in accordance with an embodiment. The planning window 500 may include three views 502, 504, and 506 that may be generated from the volume or shape data. The views 502, 504, and 506 may show the patient's acetabulum 508 along different anatomical planes. For example, the three views may be 2D images and may correspond to coronal, sagittal, and axial views. The views may be generated by making cuts through a center point of the volume or shape data. Controls, such as moveable lines, may be provided in the views, and a user may drag a line to change where a cut is made, thereby changing the view being presented on the acetabulum. The views 502, 504, and 506 may be synchronized with each other as the user moves through the volume or shape data. It should be understood that other views, for example based on different cuts, may be generated. In some embodiments, a 3D surface model may also be presented in the planning window 500.

A digital template 510 of a selected acetabular cup may be superimposed at the acetabulum 508. The digital template 510 may be placed in the acetabulum 508 and moved to a desired position and a desired orientation. For example, controls may be included in one or more of the views 502, 504, and 506 for moving the digital template 510 relative to the acetabulum 508. For example, each view 502, 504, and 506 may include a move up button 512, a move fast up button 514, a move left button 516, a move fast left button 518, a move down button 520, a move fast down button 522, a rotate clockwise button 524, a rotate counterclockwise button 526, a move right button 528, and a move fast right button 530. One or more planning views, such as the planning view 504, may further include zoom in and zoom out buttons, such as a zoom in button 532 and a zoom out button 534. The planning window 500 may be presented on a touchscreen surface, and the buttons may be selected by touch. In other embodiments, the buttons may be selected by placing a cursor on a desired button, and selecting the desired button, e.g., using a mouse, a stylus, or other input device.

Figure 6:
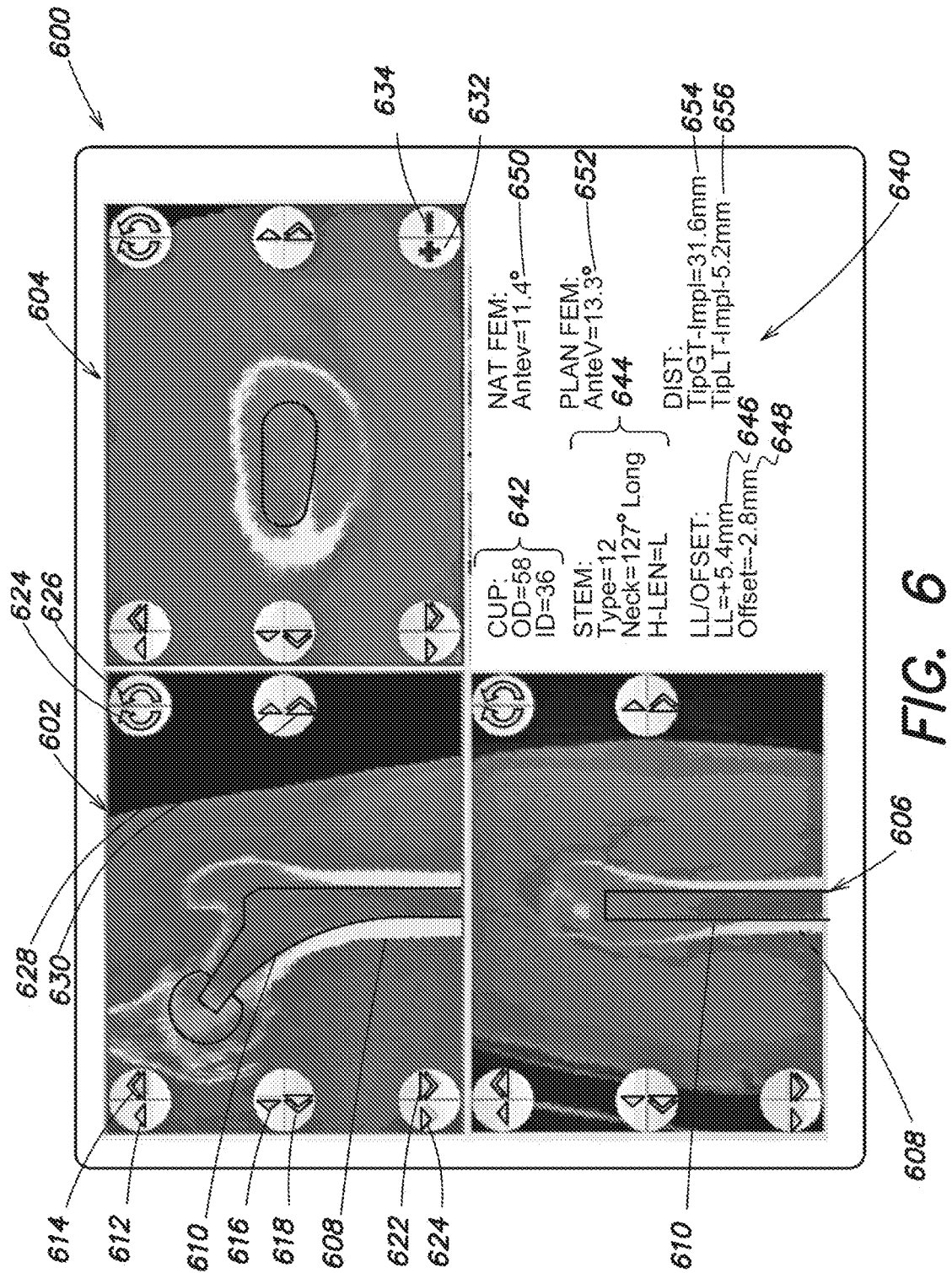
FIG. 6 is a schematic illustration of an example planning window in accordance with one or more embodiments.

FIG. 6 is a schematic illustration of an example of another planning window 600, which may be generated by the UI engine 302 of the surgical planning system 300, in accordance with an embodiment. The planning window 600 may include three views 602, 604, and 606 that may be generated from the volume or shape data. The views 602, 604, and 606 may show different views of the patient's femur 608, e.g., coronal, sagittal, and axial views. One or more digital templates of selected femoral components, such as digital template 610, may be superimposed on the femur 602. As with the digital template 510 of the acetabular cup, the digital template 610 of the femoral component may be moved relative to the femur 602 to a desired position and orientation. For example, as with the planning window 500, the views 602, 604, and 606 may include controls for moving the digital template 610 relative the femur 608, such as a move up button 612, a move fast up button 614, a move left button 616, a move fast left button 618, a move down button 620, a move fast down button 622, a rotate clockwise button 624, a rotate counterclockwise button 626, a move right button 628, a move fast right button 630, a zoom in button 632 and a zoom out button 634.

The planning window 600 also may include an outcome area 640. The outcome area 640 may display values computed by the surgical planning system 300, and other information. For example, the outcome area 640 may include acetabular cup component data 642, which may include the outside diameter (OD) and the inside diameter (ID) of the selected acetabular cup component. The outcome area 640 may include hip stem component data 644, which may include the stem type, neck length, neck inclination, and prosthetic femoral head length. The outcome area 640 also may include change values and other data computed by the evaluation tool 308. For example, the outcome area 640 may include a computed change in leg length 646 and a computed change in offset 648. The outcome area 640 also may include a native femur anteversion value 650 and a planned femur anteversion value 652.

The outcome area 640 may also include one or more virtual distances computed by the evaluation tool 308. For example, the outcome area 640 may include a first virtual distance 654, which may be the computed distance between the greater trochanter (GT) of the patient's femur and the shoulder of the femoral component, and a second virtual distance 656, which may be the computed distance between the lesser trochanter (LT) of the patient's femur and the shoulder of the femoral component. The first virtual distance 654 may be labeled Tip of Greater Trochanter to Implant (TipGT-Impl). The second virtual distance 656 may be labeled Tip of Lesser Trochanter to Implant (TipLT-Impl).

The planning windows 500 and 600 are meant for illustrative purposes only. It should be understood that other user interfaces having additional or other user interface elements may be generated and used.

The planning windows 500 and 600, including the outcome area 640, may be included in the surgical plan 316.

Figure 7:
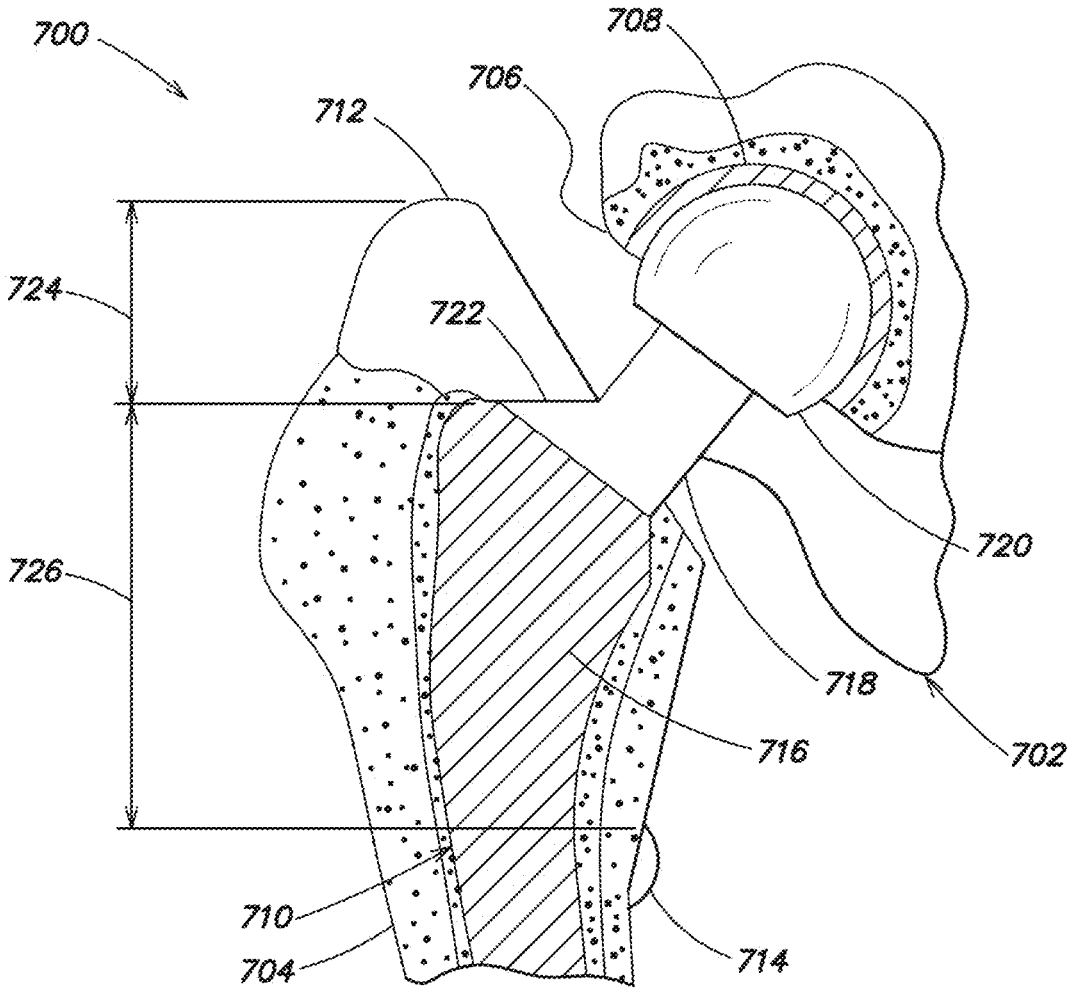
FIG. 7 is a schematic illustration of a portion of a hip with example hip components implanted therein in accordance with one or more embodiments.

FIG. 7 is schematic illustration of a portion 700 of a hip with implanted hip components. The hip portion 700 includes a portion of a pelvis 702 and a portion of a femur 704. The pelvis portion 702 includes an acetabulum 706. An acetabular cup component 708 may be implanted in the acetabulum 706. A femoral component 710 may be implanted in the femur portion 704. The femur portion 704 has a greater trochanter 712 and a lesser trochanter 714. The femoral component 710 may include a femoral hip stem 716, a neck 718, and a head 720. The neck 718 may have a shoulder 722. In some embodiments, the shoulder may be formed on the femoral hip stem 716.

Reference number 724 illustrates a distance or depth between the shoulder 722 of the neck 718 and the greater trochanter 712, for example to a top of the greater trochanter 712. Reference number 726 illustrates a distance or depth between the shoulder 722 and the lesser trochanter 714, for example to a top of the lesser trochanter 714. In some embodiments, the distance 724 may be between a first transverse plane that includes the shoulder 722 and/or a point thereon and a second transverse plane that includes the greater trochanter 712 and/or a point thereon. For example, the distance between the first and second transverse planes may be longitudinal even though the two points are not aligned longitudinally. In some embodiments, the distance 726 may be between the first transverse plane that includes the shoulder 722 and/or a point thereon and a third transverse plane that includes the lesser trochanter 714 and/or a point thereon. Again, the distance between the first and third transverse planes may be longitudinal even though the two points are not aligned longitudinally. In some embodiments, the first and second distances 724, 726 may be within one or more sagittal, e.g., lateral, planes.

It should be understood that the evaluation tool 308 may determine other or additional virtual distances. For example, one or more lateral distances may be determined. An exemplary lateral distance may be between a point on a femoral component and the lesser trochanter.

Surgery

During surgery, the surgeon may implant the planned hip components according to the surgical plan 316. FIGS. 8A-8C are partial views of a flow diagram of an example method in accordance with an embodiment. The surgeon may implant a physical hip stem component matching the planned component at the patient's femur, and may implant a physical acetabular cup component matching the planned component at the patient's acetabulum, as indicated at step 802. The surgeon may implant the hip joint components as close to the planned locations and orientations as practically possible. In some embodiments, the surgeon may determine whether the acetabular cup is positioned within the patient's acetabulum at the planned location. The surgeon may use visual cues to determine whether the cup is at the planned location. For example, the surgeon may measure the distance from the spherically reamed bed in the acetabulum to the medial depth of the acetabular notch. In addition, the surgeon may observe the appearance of the acetabular cup within the surrounding bone. If the measured distance and/or the observed appearance/location of the cup differs from planned distance or appearance/location, the digital template of the acetabular cup component may be repositioned on the plan to match the measured distance and/or the observed location/appearance of the physical cup within the bone, as indicated at step 804. While the acetabular contributions to leg length and offset may be smaller than the femoral contributions, repositioning the digital template of the acetabular cup to match the location of the physical cup component may result in more accurate calculations of acetabular contributions to leg length and offset changes by the evaluation tool 308.

The surgeon or an assistant may measure a physical distance corresponding to the one or more virtual distances computed by the evaluation tool 308, as indicated at step 806. For example, the surgeon or assistant may measure the physical longitudinal distance between the tip of the patient's greater trochanter and the shoulder of the actual hip stem component. To do this, the surgeon may place a first end of a rod, such as a ¼-inch diameter steel rod, on the shoulder of the hip stem component. The surgeon may then slide her thumb down the rod until her thumb contacts the greater trochanter. Leaving her thumb at the marked position on the rod, the rod may be removed, and the distance from the end of the rod to the point marked by the surgeon's thumb measured. In other embodiments, a surgical depth gauge or other surgical tool may be used to measure the physical distance. The surgeon or assistant may also measure the physical distance between the tip of the lesser trochanter and the neck-stem junction at the medial neck. These physical distances may be measured before a trial reduction of the hip with the hip joint components.

In some embodiments, the surgeon may have the surgical plan 316 including the planning window 500 open and accessible during the surgery, and the physical distances may be entered into the surgical plan 316. The surgical plan 316 may be opened on a data processing device, such as a laptop computer, a tablet computer, etc., and presented on the device's display. The surgeon may compare the physical distances to the planned virtual distances as computed by the evaluation tool 308, and determine whether they match, e.g., are equivalent, as indicated at decision step 808.

If the physical distances measured during surgery match the virtual distances computed during the planning stage, the surgeon may perform a trial reduction of the hip, as indicated by Yes arrow 810 leading to step 812. The surgeon may then proceed to complete the procedure, as indicated at step 814. In this case, the patient's post-surgery leg length, offset and AP position changes will closely correspond to the originally planned leg length, offset, and AP position change values.

Returning to decision step 808, suppose one or more of the measured physical distances is different, e.g., greater or lesser, than the respective virtual distance computed by the surgical planning system 300 during the planning stage. For example, suppose the planned virtual distance is 30 mm, but the measured physical distance is 25 mm. This may occur as a result of the physical femoral hip stem being positioned differently than planned. The physical distance may be entered into and/or received by the surgical planning system 300, as indicated by No arrow 816 leading to step 818. In some embodiments, the surgeon or assistant may reposition the digital template 610 for the hip stem component on the surgical plan 316, e.g., on the display of the shape or volume data, so that the shoulder of the digital template of the hip stem component is spaced from the tip of the greater trochanter a virtual distance that matches the physical distance measured during surgery. For example, the surgeon or assistant may use the move up and/or move down buttons 612 and 620 to reposition the digital template. Each selection or "click" of the move up and move down buttons 612 and 620 may correspond to a 1 mm change in position of the digital template relative to the shape or volume data. As the digital template is being moved up and down, the planning tool 306 may dynamically compute new virtual distances, which may be displayed in the outcome area 640. The surgeon or assistant may stop moving the template 610 when the newly computed virtual distance matches the physical distance measured during surgery.

In other embodiments, the first and/or second planning windows 500, 600 may include one or more controls for receiving the obtained physical distance, such as a data entry box, and the surgeon or assistant may enter the physical distances in the box. In response to receiving the physical distance, the planning tool 306 may automatically reposition the template of the stem component in the surgical plan 316 so that the virtual distance matches the measured physical distance.

With the template 610 repositioned to match the physical distance measured during surgery, the evaluation tool 308 may determine new change values for leg length, offset, and/or AP position, as indicated at step 820 (FIG. 8B). In some embodiments, the evaluation tool 308 may calculate new values in response to each move of the digital template relative to the display of the shape or volume data. The evaluation tool 308 may utilize the geometry of the hip joint components as represented by the templates when recalculating changes in leg length, offset, and/or AP position. The new leg length, offset, and/or AP position change values may be output by the surgical planning system 300, as indicated at step 822. For example, the new leg length, offset, and/or AP position change values may be displayed in the outcome area 640 of the second planning window 600 of the surgical plan 316. The evaluation tool 308 may be configured to compute and present new leg length, offset, and/or AP position change values in real time, e.g., from the perspective of the surgeon. The surgeon may determine whether the new computed leg length, offset, and/or AP position change values are acceptable, as indicated at decision step 824. For example, the planning surgeon may determine whether the new computed leg length, offset, and/or AP position change values still meet the goals set for the procedure. If they do, the surgeon may proceed with the surgery, as indicated by Yes arrow 826, leading to Go To block 828, which jumps to step 812 (FIG. 8A).

If one or more of the new computed leg length, offset, and/or AP position change values do not meet the goals set for the surgery, the surgeon may evaluate other hip components, as indicated by No arrow 830 leading to step 832. For example, the surgeon may select digital templates for other hip components, such as different neck and head combinations. The different neck and head combinations may have different angles and lengths. In response to inputs from the surgeon, the planning tool 306 may superimpose the templates on the display of the shape or volume data, move them to desired locations and orientations, and evaluate the resulting leg length, offset, and AP change values computed by the planning system 300. Even if the new leg length, offset, and AP position change values meet the goals set for the surgical procedure, the surgeon may still virtually evaluate other hip joint components to see whether the change values may be further optimized for the patient.

Following this iterative design and evaluation process, the surgeon may settle on a new set of hip joint components to be used with the patient, such as a particular femoral hip stem, a particular neck portion, and a particular femoral head, that meet the goals set for the surgery, as indicated at step 834 (FIG. 8C). In some embodiments, the depth of the femoral hip stem component may not change during the iterative design and evaluation process. Accordingly, the evaluation tool 308 may not calculate a new virtual distance. However, in other embodiments, with the digital templates for the newly selected hip components superimposed on the display of the shape or volume data in the desired positions and orientations, the evaluation tool 302 may calculate new virtual distances, as indicated at step 836.

The surgeon may implant physical components corresponding to these newly selected hip components, as indicated by Go To block 838, which leads to step 802 (FIG. 8A). In some embodiments, new physical distances may be obtained and compared to the current virtual distances.

It should be understood that the process of FIG. 8 or portions thereof may be repeated one or more times. For example, the process of FIG. 8 may represent one or more design and evaluation feedback loops that may be performed by the system 300 during the surgical procedure to optimize the selection, position, and orientation of hip components for the patient. In other words, the process of the present disclosure or portions thereof may be repeated one or more times until particular hip joint components placed at particular locations and orientations are found that meet the goals of the procedure.

Computer Model of the Hip

As described, the planning stage may utilize patient-specific volume or shape data. In other embodiments, a computer model of the patient's hip may be generated, and utilized during planning and surgical phases. FIGS. 9A and 9B are partial views of an example method in accordance with an embodiment. The modeling tool 304 may access the shape or volume data for the patient's hip, as indicated at step 902, and may generate a computer model, such as a three-dimensional (3D) surface model, of the patient's hip or a portion thereof from the volume or shape data, as indicated at step 904. The modeling tool 304 may establish one or more coordinate systems for the model of the hip, as indicated at step 905. The UI engine 302 may generate a planning window, and present it on the display 318, as indicated at step 906. The planning window may include a visual representation of the computer model. The planning window may be implemented as a Graphical User Interface (GUI) having a plurality of controls.

In response to user input, the planning tool 306 may superimpose one or more selected digital templates 312 onto the computer model of the patient's hip, as indicated at step 908. The one or more digital templates may be obtained from the data store 310, and may represent one or more hip joint components. As described, a surgeon or other medical practitioner may select digital templates 312 representing particular hip components from the data store 310. In response, the planning tool 306 may superimpose the digital templates onto the computer model. The surgeon or medical practitioner may move the digital templates 312 to desired locations and orientations relative to the computer model, e.g., within the femur and the acetabulum. In some embodiments, the modeling tool 304 may virtually reduce the computer model of the hip utilizing the selected digital templates representing the particular hip components, as indicated at step 910. For example, the modeling tool 304 may center the template for the prosthetic femoral head in the template for the acetabular cup. In other embodiments, step 910 may be omitted or performed at other times.

The evaluation tool 308 may calculate changes in leg length, offset, and/or AP position, as indicated at step 912. As described, the changes in leg length, offset, and/or AP position may be determined relative to one or more coordinate systems, such as a pelvic coordinate system and a femoral coordinate system.

Again, the process of selecting digital templates, positioning them on the computer model, and computing leg length, offset, and/or AP position change values, may be repeated, as indicated by arrow 914, which loops back from step 912 to step 908. For example, the planning surgeon may conclude that the determined changes in leg length, offset, and/or AP position do not meet the goals of the procedure. To achieve the goals, the surgeon may evaluate other hip joint components by selecting the digital templates for such other hip joint components, superimposing the templates on the computer model, and moving them to desired locations and orientations. In other cases, the planning surgeon may evaluate multiple different hip joint components and/or locations or orientations. Following this iterative design and evaluation process, the surgeon may settle on a particular set of hip joint components to be used during surgery.

With the digital templates for the desired hip components superimposed on the computer model in the desired positions and orientations, the evaluation tool 308 may determine one or more virtual distances between a landmark on the pelvis or on the femur and a portion, such as a point, on one or more of the digital templates of the hip components, as indicated at step 916 (FIG. 9B). In some embodiments, the evaluation tool 302 may determine a longitudinal distance between the greater trochanter 118 (FIG. 1) and the shoulder 215 (FIG. 2) of the template of the femoral hip stem.

The planning tool 306 may generate one or more surgical plans, such as the surgical plan 316, as indicated at step 918. The surgical plan 316 316 include the identity of the particular hip components selected for use in the surgical procedure, as well as their planned location and orientation. The surgical plan 316 also may include the computed changes in leg length, offset, and/or AP position. The surgical plan 316 may additionally include the one or more computed virtual distances. The surgical planning system 300 may output the surgical plan 316, as indicated at step 920. For example, the surgical plan 316 may be printed, saved to a memory location of a data processing device, and/or transmitted to a recipient, e.g., by email, text, or facsimile. The surgical planning stage may then be complete.

FIG. 10 is a schematic illustration of an example planning window 1000, which may be generated by the UI engine 302 of the surgical planning system 300, in accordance with an embodiment. The planning window 1000 may include a model area 1001 presenting a visual depiction of a computer model 1002 of a patient's hip. The hip model 1002 may be created by the modeling tool 304 from the volume or shape data 314 received for a patient's hip. The hip model 1002 may be a surface model, and may include a pelvis 1004, a left femur 1006, and a right femur 1008. The right femur 1008 may include a native head 1010, a greater trochanter 1012, and a lesser trochanter 1014. The hip model 1002 may be a two-dimensional (2D) model, a three dimensional (3D) model, or a combination 2D and 3D model.

FIG. 11 is a schematic illustration of the planning window 1000 with digital templates for several hip components superimposed on the hip model 1002. For example, the native femoral head of the right femur 1008 may be omitted from the hip model 1002, and a digital template 1102 of a selected femoral hip stem may be superimposed at the right femur 1008. The digital template 1102 of the femoral hip stem may include a shoulder 1103 and a neck portion 1104. In addition to the digital template 1102 of the femoral hip stem, a digital template 1106 of the femoral head may be superimposed on the hip model 1002, and a digital template 1108 of the acetabular cup may be superimposed on the hip model 1002 at the acetabulum.

In some embodiments, the planning window 1000 may include one or more drop down menus and/or palettes (not shown) from which templates for desired hip components may be selected and added to (or removed from) the model area 1001. The drop down menus and/or palettes may identify the available digital templates 312, stored in the data store 310, for example by product name or other identifying characteristic. A user may select a desired template from the drop down menu and/or palette. In response, an instance of the selected template may be placed in the model area 1001 of the planning window 1000. The user may then move the template to a desired location and orientation relative to the hip model 1002, using a cursor or other user interface elements. The planning tool 306 may lock a template in a position relative to the model 1002 once the template is positioned at a desired location and orientation for example in response to user input.

In some embodiments, the planning window 1000 may include one or more data or other display areas, such as a planning area 1110 and an outcome area 1112, in addition to the model area 1001. The UI engine 302 may configure the display areas as windows or panes. The planning area 1110 may include widgets for use in planning the surgery. For example, the planning area 1110 may include a data entry widget 1114 for receiving and/or presenting a patient name, first and second widgets 1116 and 1118, such as sliders, + and – buttons, and numeric entry boxes through which operative anteversion and operative inclination values, respectively, may be received and/or presented, and a data entry widget 1120 for receiving and/or presenting a pelvic tilt value. The planning tool 306 may compute the supine pelvic tilt, for example from the position of the AP Plane with the patient supine in the CT coordinate space. In some embodiments, a standing pelvic tilt parameter, as measured on preoperative assessment such as lateral radiographs of simultaneous biplane radiographs may be entered and added. This may create a "functional" pelvic coordinate space and acetabular cup angles may be measured relative to the functional coordinate system instead of the AP Plane coordinate system or relative to any other coordinate system that the surgeon may find useful.

The planning area 1110 also may include planning tabs, such as a Cup Plan tab 1122 and a Stem Plan tab 1124. The Stem Plan tab 1124, which is illustrated in FIG. 11, may include widgets for selecting and planning the stem components. For example, the Stem Plan tab 1124 may include a Family drop down box 1126 through which a user may select a family of stem components, e.g., by manufacturer and/or product name. The Stem Plan tab 1124 also may include drop down boxes 1127-1130 for selecting a prosthetic femoral head diameter, a head length, a neck type, and a femoral hip stem size, respectively. Depending on the type of femoral stem component, the Stem Plan tab 1124 also may include a check box 1131 to indicate whether reduced flare is being used. For example, the Profemur Renaissance Hip Stem System from MicroPort Scientific Corp. of Arlington, TN includes femoral hip stem components having either standard or reduced flares. It should be understood that other widgets may be used to select or identify characteristics of the planned hip joint components. In some embodiments, templates may be selected in response to the entry of desired values in the drop down boxes 1126-1131. For example, as indicated by values included in the drop down boxes, 1127-1130, a hip stem having a head diameter of 36, a medium (M) head length, a 127° medium neck type, and a stem size of 14 may be selected. Instances of the templates may be presented in the model area 1001 portion of the planning window 1000, and moved to desired locations and orientations relative to the hip model 1002.

The Stem Plan tab 1124 also may include a command button 1134 that, if selected causes the modeling tool 304 to virtually reduce the digital templates of the prosthetic femoral head with the templates for the acetabular cup and liner (if used). For example, the modeling tool 304 may reposition the digital templates of the prosthetic femoral head, neck portion, and femoral hip stem such that the prosthetic femoral head is centered in the digital template for the acetabular cup component.

The outcome area 1112 may include fields for presenting one or more values at least some of which may be computed by the surgical planning system 300 for the surgical plan being prepared. For example, the outcome area 1112 may include a data field 1136 for presenting acetabular cup component data, such as the outside diameter (OD) and inside diameter (ID) of the selected cup component. The outcome area 1112 may include a data field 1138 for presenting stem component data, such as stem type, neck length, neck inclination, and prosthetic femoral head length. The outcome area 1112 also may include fields for presenting change values and other data computed by the evaluation tool 308. For example, the outcome area 1112 may include widgets, such as numeric display elements, for presenting computed changes in leg length 1140, offset 1142, and AP position 1144. The outcome area 1112 also may include fields 1146 and 1148 for presenting native femur anteversion and planned femur anteversion, respectively. The outcome area 1112 may also include other widgets that present one or more virtual distances computed by the evaluation tool 308. For example, the outcome area 1112 may include a field 1150 for presenting a first virtual distance (TipGT-Impl), which may be the computed distance between the greater trochanter (GT) 1012 and the shoulder 1103 of the hip stem component 1102, and a field 1152 for presenting a second virtual distance (TipLT-Impl), which may be the computed distance between the lesser trochanter (LT) and the shoulder 1103 of the hip stem component 1102.

It should be understood that the planning window 1000, including the data included in the planning window 1000, may represent a surgical plan 316.

Surgery

As discussed herein, during surgery, the surgeon may implant the planned hip components. The surgeon may also access the surgical plan 316.

Suppose that, during surgery, physical distances of 29 mm from the greater trochanter and 11 mm from the lesser trochanter are measures.

FIG. 12 is a schematic illustration of the planning window 1000 in accordance with an embodiment. In this figure, the digital template 1102 of the femoral hip stem is repositioned to match the physical distance(s) measured during surgery. For example, the digital template 1102 of the femoral stem is moved down relative to the femur 1008 so that the shoulder 1103 of the femoral stem is now 29 mm from the greater trochanter 1012, and 11 mm from the lesser trochanter, thereby matching the physical distances measured during surgery. The evaluation tool 308 may present these new distances at fields 1202 and 1204. With the digital template 1102 of the stem moved to this new location, the evaluation tool 308 may compute new change values for leg length, offset, and AP position, e.g., 5.8 mm, 0.9 mm, and 2.1 mm, respectively. These new change values may be presented in the outcome area 1112 of the planning window 1000, as indicated at fields 1206, 1208, and 1210, respectively.

As described, the surgeon may determine whether these new computed values meet the goals set for the procedure. If so, the surgical procedure may proceed with the femoral hip stem at the present location. If not, for example if one or more of the new computed values for leg length, offset, and/or AP position are not acceptable, the surgeon may enter a planning update phase. For example, 10 mm or more in leg length change is typically not optimal for most patients.

Suppose, for example, that the surgeon wants to evaluate a short neck portion, e.g., instead of the medium neck portion as planned. The surgeon or assistant may select corresponding digital templates and superimpose them on the hip model 1002.

FIG. 13 is a schematic illustration of the planning window 1000 in accordance with an embodiment. The planning window 1000 includes the hip model 1002 in the model area 1001. In this embodiment, a digital template 1302 of a femoral hip stem with a short neck portion 1304 is presented, instead of the planned medium length neck 1104 (FIG. 11). For example, as indicated by values presented in the drop down boxes, 1306, 1308, 1310, and 1312, the surgeon may select, e.g., for evaluation, a hip stem having a short(S) head length, a 127° short neck type, a stem size of 14, and reduced flare. Information on the new hip stem selected for evaluation may be presented in a data field 1314 of the outcome area 1112. As described, the surgeon may place the template(s) for the new hip stem 1302 in desired locations and orientations at the model 1002 of the patient's hip. The evaluation tool 308 may compute leg length, offset, and AP change values for the new hip stem 1302, and present these change values at fields 1316, 1318, and 1320, respectively. The evaluation tool 308 also may compute one or more virtual distances for the new hip stem 1302, and present them at fields 1322 and 1324. If the leg length, offset, and AP change values computed for the new hip stem 1302 meet one or more goals for the surgery, the surgeon may implant physical components corresponding to this new hip stem.

Alternatively or additionally, the surgeon may wish to evaluate other components, such as a long neck portion. The surgeon or assistant may select corresponding digital templates and superimpose them on the hip model 1002.

FIG. 14 is a schematic illustration of the planning window 1000 in accordance with an embodiment. The planning window 1000 includes the hip model 1002 in the model area 1001. In this embodiment, a digital template 1402 of a femoral hip stem having a long neck portion 1402 is presented. For example, as indicated by values presented in the drop down boxes, 1406, 1408, 1410, and 1412, the surgeon may select, e.g., for evaluation, a hip stem having a long (L) head length, a 127° long neck type, a stem size of 14, and reduced flare. Information on the new hip stem selected for evaluation may be presented in a data field 1414 of the outcome area 1112. As described, the surgeon may place the template(s) for the new hip stem 1402 in desired locations and orientations at the model 1002 of the patient's hip. The evaluation tool 308 may compute leg length, offset, and AP change values for the new hip stem 1402, and present these change values at fields 1416, 1418, and 1420, respectively. The evaluation tool 308 also may compute one or more virtual distances for the new hip stem 1402, and present them at fields 1422 and 1424. If the leg length, offset, and AP change values computed for the new hip stem 1402 meet one or more goals for the surgery, the surgeon may implant physical components corresponding to this new hip stem.

It should be understood that FIGS. 11-14 are meant for illustrative purposes only, and represent just three possible design alternatives. The surgeon may also or alternatively evaluate different design alternatives, such as different neck types, neck angles, etc. For example, while FIGS. 11-14 illustrate hip stems having short, medium, and long head lengths, some families of hip stems may only be available in short and long head lengths. With respect to heads, they may be available in short, medium, long, extra-long, and extra extra-long sizes. Other head sizes that may be available are −4, 0, 4, 8, and 12 mm. Stems may be available in standard, offset, and high offset sizes, in which case the neck may not be changed by angle per se, but the neck may provide a pure increase in offset without adding length. For example, an available size may be 8 mm straight sideways. It should be understood that the present disclosure may be used with templates and physical hip components of any sizes, configurations, and/or shapes.

In some embodiments, a planning window may use both 2D views of volume and shape data and a computer model. For example, planning and evaluation of femoral components may be performed using 2D views of volume and shape data, while planning and evaluation of acetabular components may be performed using a computer model of the hip.

Digitizing Points on Templates of Hip Components

In some embodiments, the evaluation tool 308 may utilize one or more points marked on the templates of the hip components to compute the virtual distances. For example, a user may direct the modeling tool 304 to open a template file for a hip component. The user may then mark one or more points on the template. The evaluation tool 308 may utilize these points when computing virtual distances, e.g., between the marked point on the template and the greater trochanter and/or lesser trochanter.

FIG. 16 is a schematic illustration of an example computer aided design (CAD) drawing of a femoral hip stem in accordance with an embodiment. The CAD drawing may be opened by the modeling tool 304 in an editor window 1600. The editor window 1600 may include a drawing area 1602 and a data area 1604. The modeling tool 304 may present a three dimensional (3D) model 1606 of the femoral hip stem in the drawing area 1602. The data area 1604 may include user interface elements for receiving and/or presenting information about the femoral hip stem illustrated in the drawing area 1602. For example, the data area 1604 may include a data entry field 1608 for receiving and/or presenting information about the implant type of the femoral hip stem, e.g., "long-straight". The data area 1604 may further include another data entry field 1610 for receiving and/or presenting information about the stem size of the femoral hip stem, e.g., "01". One or more controls, indicated at 1612, may be provided in the editor window 1600. The controls 1612 may be used to manipulate how the 3D model 1606 is rendered in the drawing area 1602. For example, the controls 1612 may be used to rotate, move, and resize the 3D model 1606, among other operations.

A user may mark a point on the 3D model 1606, and this marked point may then be used by the planning tool 306, for example when calculating virtual distances to the greater trochanter and/or the lesser trochanter. For example, the 3D model may include a neck portion 1614, and the neck portion 1614 may include a shoulder 1616. A user may mark a point 1618 on the shoulder of the 3D model 1606. The modeling tool 304 may capture the coordinates of the point 1618, for example the x, y, z coordinates of the point 1618 in a coordinate system for the 3D model 1606. The marking of the point 1618 may be referred to as digitizing a point on the 3D model 1606. In some embodiments, the user may mark additional points on the 3D model 1606. For example, the user may mark another point 1620 on the 3D model 1606.

If the 3D model 1606 is used in the planning stage for a hip procedure, the planning tool 306 may utilize the marked point, e.g., the point 1618 on the shoulder 1616, when computing virtual distances to the greater trochanter and/or the lesser trochanter. In some embodiments, the planning tool 306 and/or the modeling tool 304 may translate the coordinates of the marked point 1618 from the local coordinate system for the 3D model 1606 to the coordinate system established for the pelvis and/or for the femur.

It should be understood that points may be similarly marked on 3D models for other hip components and/or on other templates, such as 2D templates of hip components.

Example Data Processing Device

FIG. 15 is a schematic illustration of an example data processing device 1500 in accordance with an embodiment. The data processing device 1500 may include one or more processors or other processing logic, such as a central processing unit (CPU) 1502, a main memory 1504, one or more storage devices, such as a disk drive 1506, a removable medium drive 1508, and one or more network interface cards (NICs) 1510 that are interconnected by one or more busses, such as a system bus 1512. The main memory 1504 may store a plurality of programs, libraries or modules, such as an operating system 1514, and one or more applications running on top of the operating system 1514, such as the surgical planning system 300. The removable medium drive 1508 may be configured to accept and read a computer readable medium 1518, such as a CD, DVD, floppy disk, solid state drive, tape, flash memory or other medium. The removable medium drive 1508 may further be configured to write to the computer readable medium 1518.

The data processing device 1500 also may include and/or be accessible by user input/output (I/O) 1520. The user I/O 1520 may include one or more of a keyboard 1522, a pointing device, such as a mouse 1524, and a display 1526. It should be understood that other or additional user I/O may be provided, such as a touch screen, a touch pad, a pen, etc.

Suitable data processing devices include servers, personal computers (PCs), workstations, laptops, palm computers, smart phones, tablet computers, etc.

Suitable operating systems 1514 include the Windows series of operating systems from Microsoft Corp. of Redmond, WA, the Linux operating system, the MAC OS® series of operating systems from Apple Inc. of Cupertino, CA, and the UNIX® series of operating system, among others.

It should be understood that the data processing device 1500 of FIG. 15 is meant for illustrative purposes only, and that the present disclosure may be used with other data processing devices, computer systems, processing systems or computational devices.

The foregoing description of embodiments is intended to provide illustration and description, but is not intended to be exhaustive or to limit the invention to the precise form disclosed. Modifications and variations are possible in light of the above teachings or may be acquired from a practice of the invention. For example, while a series of acts has been described above with respect to the flow diagrams, the order of the acts may be modified in other implementations. Further, non-dependent acts may be performed in parallel. In addition, the term "user", as used herein, is intended to be broadly interpreted to include, for example, a computer or data processing system or a user of a computer or data processing system, unless otherwise stated.

Further, certain embodiments of the invention may be implemented as logic that performs one or more functions. This logic may be hardware-based, software-based, or a combination of hardware-based and software-based. Some or all of the logic may be stored in one or more tangible non-transitory computer-readable storage media and may include computer-executable instructions that may be executed by a computer or data processing system, such as server system 102. The computer-executable instructions may include instructions that implement one or more embodiments of the invention. The tangible non-transitory computer-readable storage media may be volatile or non-volatile and may include, for example, flash memories, dynamic memories, removable disks, and non-removable disks.

No element, act, or instruction used herein should be construed as critical or essential to the invention unless explicitly described as such. In addition, as used herein, the article "a" is intended to include one or more items. Where only one item is intended, the term "one" or similar language is used. Further, the phrase "based on" is intended to mean "based, at least in part, on" unless explicitly stated otherwise.

The foregoing description has been directed to specific embodiments of the present invention. It will be apparent, however, that other variations and modifications may be made to the described embodiments, with the attainment of some or all of their advantages. Therefore, it is the object of the appended claims to cover all such variations and modifications as come within the true spirit and scope of the disclosure.

What is claimed is:

1. A method comprising:

displaying, on a display screen, an image of at least a portion of a hip of a patient;

superimposing at least one digital template of a hip component on the image at a planned location relative to the at least a portion of the hip;

with the at least one digital template of the hip component superimposed on the image at the planned location, determining, by a processor, a baseline value for at least one of a leg length, an offset, or an anterior-posterior (AP) position for the hip, wherein the baseline value is determined by summing a femoral contribution to the at least one of the leg length, the offset, or the anterior-posterior (AP) position and an acetabular component to the at least one of the leg length, the offset, or the anterior-posterior (AP) position;

with the at least one digital template of the hip component superimposed on the image at the planned location, determining, by the processor, a planned distance between (i) an anatomical landmark on the image and (ii) a location on the hip component included in the at least one digital template;

outputting the baseline value and the planned distance;

receiving a measurement of a physical distance between (i) a physical anatomical landmark on the hip, wherein the physical anatomical landmark corresponds to the anatomical landmark on the image, and (ii) a physical location on a physical hip component implanted at the hip of the patient, wherein the physical location corresponds to the location on the hip component included in the at least one digital template, the physical distance being different than the planned distance;

repositioning the at least one digital template of the hip component on the image or on a second image of the at least a portion of the hip to match the physical distance between the physical anatomical landmark and the physical location on the physical hip component as measured;

determining, by the processor, a change value in the at least one of the leg length, the offset, or the AP position, wherein the change value is based upon the at least one digital template of the hip component being repositioned on the image or on the second image to match the physical distance as measured; and outputting the change value in the at least one of the leg length, the offset, or the AP position.

2. The method of claim 1 wherein the at least one digital template of the hip component represents at least one of:

a broach;

a femoral hip stem;

a prosthetic neck portion;
a prosthetic femoral head;
an acetabular cup; or
an acetabular liner.

3. The method of claim 1 wherein the at least one digital template of the hip component includes a first digital template of a hip stem component and a second digital template of an acetabular cup component.

4. The method of claim 3 further comprising:
performing a virtual trial reduction utilizing the first digital template and the second digital template.

5. The method of claim 1 wherein the at least one digital template includes a hip stem component and further wherein the anatomical landmark is a greater trochanter or a lesser trochanter and the location on the hip component shown on the at least one digital template is a shoulder of the hip stem component.

6. The method of claim 1 wherein the image of the at least a portion of the hip includes a three-dimensional (3D) model.

7. The method of claim 1 further comprising:
superimposing a second digital template of a second hip component on the image or on the second image of the at least a portion of the hip for evaluating the second hip component;
determining, by the processor, a revised baseline value in the at least one of the leg length, the offset, or the anterior-posterior (AP) position, wherein the revised baseline value is based upon a substitution of the at least one digital template of the hip component with the second digital template of the second hip component that is different from the hip component included in the at least one digital template; and
outputting the revised baseline value.

8. The method of claim 7 further comprising:
determining, by the processor, a revised planned distance between the anatomical landmark on the image or on the second image of the at least a portion of the hip and a location on the second hip component included on the second digital template; and
outputting the revised planned distance.

9. The method of claim 1 further comprising:
establishing one or more coordinate systems at the at least a portion of the hip, wherein the one or more coordinate systems is at least one of pelvic coordinate system, a femoral coordinate system or a functional coordinate system.

10. The method of claim 1 further comprising:
receiving an indication of the location on the hip component included in the at least one digital template.

11. An apparatus comprising:
a memory storing a plurality of digital templates of hip components;
a first display; and
one or more processors coupled to the memory and the first display, the one or more processors configured to:
display, on the first display, an image of at least a portion of a hip;
superimpose on the image a selected digital template of a hip component from the plurality of digital templates at a planned location relative to the at least a portion of the hip;
with the selected digital template of the hip component superimposed on the image at the planned location, determine a baseline value for at least one of a leg length, an offset, or an anterior-posterior (AP) position for the hip, wherein the baseline value is determined by summing a femoral contribution to the at least one of the leg length, the offset, or the anterior-posterior (AP) position and an acetabular component to the at least one of the leg length, the offset, or the anterior-posterior (AP) position;
with the selected digital template of the hip component superimposed on the image at the planned location, determine a planned distance between (i) an anatomical landmark on the image and (ii) a location on the hip component shown on the selected digital template;
output, on the first display, the baseline value and the planned distance;
with a physical hip component implanted at the hip of the patient, reposition the selected digital template of the hip component on the image to match the physical distance between the physical anatomical landmark and the physical location on the physical hip component based on a value representing a distance between (i) a physical anatomical landmark on the hip, wherein the physical anatomical landmark corresponds to the anatomical landmark on the image, and (ii) a physical location on the physical hip component, wherein the physical location corresponds to the location on the hip component shown on the selected digital template;
determine a change value in the at least one of the leg length, the offset, or the AP position, wherein the change value is based upon the selected digital template of the hip component being repositioned on the image to match the physical distance as measured; and
output, on the first display or on a second display, the change value in the at least one of the leg length, the offset, or the AP position.

12. The apparatus of claim 11, wherein the selected digital template of the hip component represents a hip stem component, and the anatomical landmark is a greater trochanter or a lesser trochanter and the location on the hip component shown on the selected digital template is a shoulder of the hip stem component.

13. The apparatus of claim 11, wherein the one or more processors are further configured to:
superimpose, on the first display or on the second display, a second digital template of a second hip component on the image of the at least a portion of the hip or on a second image of the at least a portion of the hip for evaluating the second hip component;
determine a revised baseline value in the at least one of the leg length, the offset, or the anterior-posterior (AP) position, wherein the revised baseline value is based upon a substitution of the selected digital template of the hip component with the second digital template of the second hip component that is different from the hip component included in the selected digital template; and
output, on the first display or on the second display, the revised baseline value.

14. The apparatus of claim 13, wherein the one or more processors are further configured to:
determine a revised planned distance between the anatomical landmark on the image or on the second image of the at least a portion of the hip and a location on the second hip component included on the second digital template; and
output, on the first display or on the second display, the revised planned distance.

15. The apparatus of claim 11, wherein the selected digital template of the hip component represents at least one of:

a broach;

a femoral hip stem;

a prosthetic neck portion;

a prosthetic femoral head;

an acetabular cup; or an acetabular liner.

16. The apparatus of claim 11, wherein the one or more processors are further configured to determine the updated change value in real-time.

17. The apparatus of claim 14 wherein the hip component shown on the template is three-dimensional (3D).

* * * * *